US009028758B2

(12) United States Patent
Keinan et al.

(10) Patent No.: US 9,028,758 B2
(45) Date of Patent: May 12, 2015

(54) SUBSTANCE DETECTOR WITH CYCLONE

(75) Inventors: Alex Keinan, Rishon-LeZion (IL);
Yevgeny Miroshnichenko,
Rishon-LeZion (IL); Mark Paradny,
Bat-Yam (IL)

(73) Assignee: Explodet Technologies Ltd.,
Hod-HaSharon (IL)

( * ) Notice: Subject to any disclaimer, the term of this patent is extended or adjusted under 35 U.S.C. 154(b) by 321 days.

(21) Appl. No.: 12/647,009

(22) Filed: Dec. 24, 2009

(65) Prior Publication Data
US 2011/0159596 A1 Jun. 30, 2011

(51) Int. Cl.
G01N 33/22 (2006.01)
B04C 9/00 (2006.01)
B04C 3/06 (2006.01)
G01N 1/22 (2006.01)
G01N 1/02 (2006.01)

(52) U.S. Cl.
CPC ........ *G01N 1/2211* (2013.01); *B04C 2009/008* (2013.01); *B04C 3/06* (2013.01); *B04C 2009/004* (2013.01); *G01N 2001/022* (2013.01); *G01N 2001/2223* (2013.01)

(58) Field of Classification Search
CPC .. G01N 1/2211; B04C 3/06; B04C 2009/004; B04C 2009/008
See application file for complete search history.

(56) References Cited

U.S. PATENT DOCUMENTS

| 5,648,047 | A | 7/1997 | Kardish et al. |
| 5,679,580 | A | 10/1997 | Ball et al. |
| 5,861,316 | A | 1/1999 | Cage et al. |
| 5,914,454 | A | 6/1999 | Imbaro et al. |
| 6,103,534 | A * | 8/2000 | Stenger et al. .......... 436/63 |
| 6,532,835 | B1 | 3/2003 | Saaski et al. |
| 6,688,187 | B1 | 2/2004 | Masquelier |
| 6,828,795 | B2 * | 12/2004 | Krasnobaev et al. ......... 324/464 |
| 6,978,657 | B1 | 12/2005 | Baumann et al. |
| 2005/0269254 | A1 * | 12/2005 | Roitman ................ 210/252 |
| 2006/0081073 | A1 | 4/2006 | Vandrish et al. |
| 2008/0171398 | A1 | 7/2008 | Tanielian |
| 2011/0132108 | A1 * | 6/2011 | Novosselov et al. ....... 73/863.22 |

FOREIGN PATENT DOCUMENTS

| WO | WO 00/69568 | 11/2000 |
| WO | WO 2007/064313 | 6/2007 |

OTHER PUBLICATIONS

International Search Report and the Written Opinion Dated Apr. 26, 2011 From the International Searching Authority Re. Application No. PCT/IL2010/001081.
Response Dated Oct. 23, 2011 to International Search Report and the Written Opinion Dated Apr. 26, 2011 From the International Searching Authority Re. Application No. PCT/IL2010/001081.

(Continued)

*Primary Examiner* — Yelena G Gakh
*Assistant Examiner* — Michelle Adams

(57) ABSTRACT

Apparatus for detecting substances in an air sample, the apparatus including: a source of air pressure differential; a cyclone connected to the source of air pressure differential; an air input port connected to the cyclone, to receive the air sample; a substance output port connected to the cyclone, to receive the substances; an input port configured to disperse a finely separated material so that it mixes with said sample; and a detector located at the substance output port, to detect a chemical change in at least one of the substances and the finely separated material.

47 Claims, 11 Drawing Sheets

(56) References Cited

OTHER PUBLICATIONS

International Preliminary Report on Patentability Dated Apr. 24, 2012 From the International Preliminary Examining Authority Re. Application No. PCT/IL2010/001081.

Notification Concerning Informal Communications With the Applicant Dated Apr. 10, 2012 From the International Preliminary Examining Authority Re. Application No. PCT/IL2010/001081.

Communication Pursuant to Article 94(3) EPC Dated Jul. 3, 2014 From the European Patent Office Re. Application No. 10803267.3.

* cited by examiner

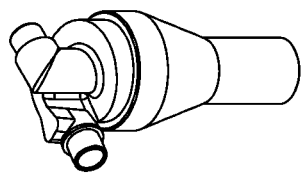
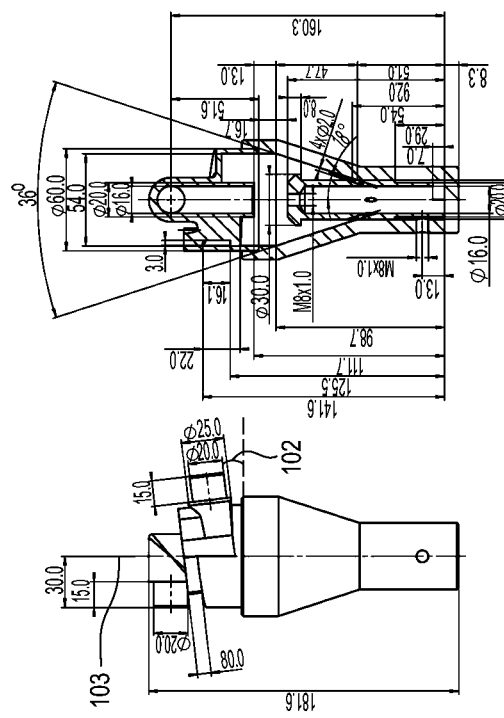
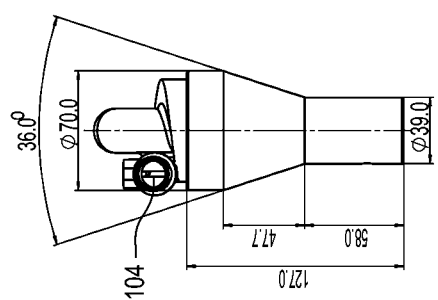
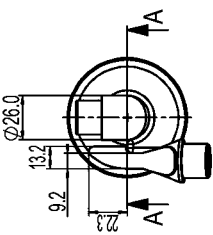
FIG. 13A  FIG. 13B  FIG. 13C  FIG. 13D  FIG. 13E

SUBSTANCE DETECTOR WITH CYCLONE

FIELD AND BACKGROUND OF THE INVENTION

The present invention, in some embodiments thereof, relates to detecting systems, and more particularly, but not exclusively, to a device and method useful for detecting certain concealed and non-visible substances, possibly at low amounts thereof.

In many public and commercial establishments there is a need to detect the presence of harmful or illegal substances in order to maintain public order, safety, and/or health. Some examples from the field of security include the detection of hidden explosives, hazardous materials, and/or illegal narcotics transported by criminals and terrorists, either on their body or in luggage or cargo. Some health and safety examples include the detection of unsafe levels of air pollution, toxic gases in an industrial environment, and pesticides at a food production/processing facility. Often more than one type of substance needs to be detected. For example, at airports and border crossings security personnel seek to intercept both explosives and illegal narcotics.

The development of an automated substance detector raises a number of technical issues. For example, the substances to be detected may have physical characteristics and chemical signatures that vary over a very wide range. In some cases the parameters to be detected may be extremely low. For example, some plastic explosives and narcotics, particularly when sealed in luggage, have vapor pressures measured in parts per billion or trillion, which is so low as to be virtually undetectable by conventional instrumentation. In order to check people in transit, the detection needs to be not only accurate but also continuous, quick, safe, and unobtrusive. It is also beneficial for such a system to be relatively low cost and compact, so that it may be cost-effectively deployed at sites that are usually unguarded or that have comparatively low traffic, such as schools and shopping centers.

Radiation technology such as x-rays or gamma rays is sometimes employed to detect concealed explosives and drugs. This technology however cannot be used to check people because of the harmful effects of radiation on health. It is also relatively inaccurate, because it can only identify the specific weight or outline of a shape of detected objects, or spectral behavior of some substances, under limited conditions. This result often at most informs the operator that objects have been detected that are potentially dangerous, and accordingly falls short of the more definitive assessment generally required to efficiently process the movement of multiple objects in real time.

Another approach, sometimes called "smeller" technology, takes an actual physical sample from the person or object being checked and/or from his immediate vicinity. The sample is analyzed to determine its chemical composition or the presence of ions of the prohibited items, such as explosives or drugs. Examples of this technology include ion mobility spectrometry and gas chromatography. Smeller systems however are generally costly and complicated to operate. Further, they can have trouble checking a continuous flow of people or objects due to the need to take samples and to be re-set between subjects.

Some attempts have been made in the art to provide automatic detectors of explosives and narcotics. Vandrish, U.S. Pat. App. 2006/0081073, shows an examination station equipped with several air jets and corresponding collection ports. Detection occurs by directing pressurized air at the subject, collecting and concentrating the air in a device such as a cyclone, and producing samples for chemical analysis. The main analysis method described is chemiluminescence, in which luminol reacts with $NO_2$ to produce optically detectable light.

Kardish, U.S. Pat. No. 5,648,047, shows a handheld manual device suitable for use by non-skilled operators. The device has an enclosed housing, a roll of substrate, and one or more reagents that can be selectively dripped onto the substrate inside the housing. A sample is taken by wiping a surface of an object to be tested on a clean segment of the substrate. The segment is then rolled to a position where the reagents can be dispensed. If explosive or narcotic chemicals are present, a reaction will occur which produces a color change (colorimetric detection) in the substrate that can be viewed by the operator.

Baumann, U.S. Pat. No. 6,978,657, shows a portable device having a metal fiber or sheet substrate. A sample is deposited on the substrate by shooting a jet of gas on the object being tested or by directly wiping a surface of the object with the substrate. The substrate is heated, and a reaction takes place if the tested chemicals are present. A gas is then passed over the substrate to carry the heated sample to a detector.

SUMMARY OF THE INVENTION

In accordance with an exemplary embodiment of the invention, there is provided a material detection system using a cyclone for extracting material(s) of interest of a sample. In an exemplary embodiment of the invention, a fluid is used to mix with and/or help with the extraction, optionally as a spray of droplets. Optionally, the fluid includes a reagent. Optionally or alternatively, a detector includes a solid reagent or reagent for interaction with the material(s) and/or reagent. In an exemplary embodiment of the invention, the cyclone is designed to optimize the extraction and/or detection of the materials.

There is provided in accordance with an exemplary embodiment of the invention, apparatus for detecting substances in an air sample, the apparatus comprising:

a source of air pressure differential, a cyclone connected to the source of air pressure differential, an air input port connected to the cyclone, to receive the air sample, a substance output port connected to the cyclone, to receive the substances, an input port configured to disperse a finely separated material so that it mixes with said sample, and a detector located at the substance output port, to detect a chemical change in at least one of the substances and the finely separated material. Optionally, said finely separated material is a spray of a fluid to which said substances adsorb.

In an exemplary embodiment of the invention, said input port is into the cyclone.

In an exemplary embodiment of the invention, the apparatus is arranged so that said finely separated material is driven to a material collector of said cyclone and from said collector travels to said output port. Optionally, said collector comprises a wall of said cyclone.

In an exemplary embodiment of the invention, the apparatus is configured to gravity feed said substances to said output port.

In an exemplary embodiment of the invention, the apparatus is configured to drive said substances to said output port.

In an exemplary embodiment of the invention, said cyclone comprises a first section with faster air flow and a second section with slower air flow. Optionally, the apparatus comprises two air outlet ports, one for each of said first and second sections. Optionally or alternatively, the apparatus comprises at least one fluid reagent port into said cyclone. Optionally, said fluid reagent port is a flowing port.

In an exemplary embodiment of the invention, the apparatus comprises a damper which causes the trapping of said material in said flow in air exhausting from said cyclone.

In an exemplary embodiment of the invention, the apparatus comprises a solid reagent input port.

In an exemplary embodiment of the invention, a controller which times said dispersing and activates said detecting.

In an exemplary embodiment of the invention, wherein said cyclone is configured so that a travel time of a sample from when it first interacts chemically with a contents of the cyclone and when it reaches said detector is within a range associated with said chemical interaction.

In an exemplary embodiment of the invention, said cyclone is configured so that a travel time of a sample from when it first interacts chemically with contents of the cyclone and when it second interacts with a second chemical in said cyclone is within a range associated with said chemical interactions.

In an exemplary embodiment of the invention, said detector is an optical color detector which detects an interaction of light with said substance.

In an exemplary embodiment of the invention, at least one of said cyclone, a container of a reagent and said detector is configured for field replacement.

In an exemplary embodiment of the invention, said input port is fluidicly connected to a container of reagent.

In some exemplary embodiments of the invention, said output port is configured to control a volume of material in said port.

There is provided in accordance with an exemplary embodiment of the invention, apparatus for detecting substances in an air sample, the apparatus comprising:
a source of air pressure differential,
a cyclone connected to the source of air pressure differential,
an air input port connected to the cyclone, to receive the air sample,
a substance output port connected to the cyclone, to receive the substances,
at least one reagent input port configured to inject at least one reagent into the cyclone, and
a detector located at the substance output port, to detect a chemical change in at least one of the substances and the at least one reagent. Optionally, the at least one reagent input port comprises a first reagent input port connected to one part of the cyclone and a second reagent input port connected to a second part of the cyclone.

There is provided in accordance with an exemplary embodiment of the invention, apparatus for separating substances in an air sample, the apparatus comprising:
a source of air pressure differential,
a cyclone connected to the source of air pressure differential,
an air input port connected to the cyclone, to receive the air sample,
a substance output port connected to the cyclone, to receive the substances, and
a damper configured to guide the substances inside the cyclone towards the substance output port. Optionally, the apparatus comprises a detector located at the substance output port, to detect a chemical change in at least one of the substances and the finely separated material. Optionally or alternatively, the apparatus comprises a material input which injects material into the cyclone to which said substances attach and wherein the damper traps material in a fast air flow portion of said apparatus. Optionally or alternatively, the apparatus comprises a material input which injects material into the cyclone to which said substances attach and wherein the damper traps material in a slow air flow portion of said apparatus.

There is provided in accordance with an exemplary embodiment of the invention, apparatus for detecting substances in an air sample, the apparatus comprising:

a source of air pressure differential, a cyclone connected to the source of air pressure differential, an air input port connected to the cyclone, to receive the air sample, a substance output port connected to the cyclone, to receive the substances, a solid reagent port adapted to bring a solid reagent into contact with said substances, and a detector located at the substance output port, to detect a chemical change in the substances due to interaction with said solid reagent. Optionally, said solid reagent port is positioned adjacent said substance output port. Optionally or alternatively, the apparatus comprises a fluid input port adapted to bring a fluid reagent into contact with said substances.

In some exemplary embodiments of the invention, the solid reagent includes zinc. Optionally or alternatively, the solid reagent is in the form of a rod. Alternatively, the solid reagent is in the form of a mesh.

In some exemplary embodiments of the invention, the solid reagent includes at least one aperture adapted to be in contact with said substances.

In some exemplary embodiments of the invention, said port includes a feeder adapted to automatically feed said solid reagent into said contact.

In some exemplary embodiments of the invention, said port is positioned so that said solid reagent does not interfere with detecting by said detector.

There is provided in accordance with an exemplary embodiment of the invention, apparatus for detecting substances in an air sample, the apparatus comprising:

a source of air pressure differential, an air passageway;

an air input port connected to the passageway, to receive the air sample, a substance output port connected to the passageway, to receive the substances, a material input port configured to inject a material into the passageway to chemically interact with said substances, and a station for processing said substance after it interacts with said material, wherein said port and said passage way and said source are configured to provide a time of travel for said sample from said material port to said station commensurate with said material and said processing.

Various options include one or more of the following:

That said station comprises a detector located at the substance output port, to detect a chemical change in at least one of the substances and the fluid.

That said station comprises a second material port, to inject a second material for interacting with one or both of said substance and said material.

That the apparatus comprises a port for injecting a source of particles that attach to said substances and wherein said configuration comprises a configuration which controls a travel time of said particles.

That said configuration is adapted to be manually varied and including at least one manual actuator therefore.

That said configuration is adapted to be automatically varied and comprising at least one controller which controls said varying. Optionally, said configuration is varied by one or more of change in speed of air flow in said passageway, change in a damper position in said passageway, change in a particle size associated with said substance and/or a change in a connection between said source or said air input and said passageway.

That said passageway comprises a cyclone.

There is provided in accordance with an exemplary embodiment of the invention, a method of controlling a reaction for detection of a substance in an airflow, comprising:
 retrieving a sample;

interacting said sample with a first reagent; and controlling a travel time of said reacted sample to a second station based on said reagent, said sample and processing to be performed at said second station.

There is provided in accordance with an exemplary embodiment of the invention, a method of controlling a reaction for detection of a substance in an airflow, comprising:

retrieving a sample;

interacting said sample with a first reagent; and conveying said sample using a cyclone to a detection location, wherein said cyclone includes at least one cyclone parameter and wherein said cyclone parameter is set according to properties of said substance and said interacting, to delay a travel of said substance so that its travel time matches a desired detection at said detection location.

There is provided in accordance with an exemplary embodiment of the invention, a method of detecting substances in an air sample, the method comprising:

collecting an air sample;

interacting said sample with a plurality of particles which attach to said substances in said air sample;

applying a centrifugal force to the air sample with said particles, thereby separating out said particles;

collecting the particles, and detecting a chemical change in said particles or said substances.

In some exemplary embodiments of the invention, interacting said sample comprises spraying a fluid that dissolves the substances. Optionally or alternatively, said fluid is a reagent. Optionally or alternatively, collecting comprises collecting by flow along a solid. Optionally or alternatively, collecting comprises collecting by interfering with an airflow of said air sample. Optionally or alternatively, the method comprises interacting said substances with a reagent after separating them out. Optionally or alternatively, the method comprises interacting said substances with a reagent after said collecting.

In some exemplary embodiments of the invention, said detecting comprises detecting after sufficient particles have been collected.

There is provided in accordance with an exemplary embodiment of the invention, a method of detecting substances in an air sample, the method comprising:

collecting an air sample;

mixing said air sample with a reagent in a cyclone, so that said substances interact therewith;

collecting the interacted substances after said mixing, and detecting a chemical change in said interacted substances. Optionally, mixing comprises mixing with two reagents at different times. Optionally or alternatively, said cyclone is fast enough to separate said interacted substances from said air.

There is provided in accordance with an exemplary embodiment of the invention, apparatus for detecting substances in an air sample, the apparatus comprising:

an air inlet;

a reagent storage a mixing chamber for mixing said sample and said reagent;

a detector for detecting said substance based on a chemical reaction caused by said mixing; and a controller for controlling said apparatus, wherein at least one of said storage, mixing chamber, detector and controller are configured to be field replaceable by module replacement of a module. Optionally, said module comprises a fast connection to said apparatus. Optionally or alternatively, said fast connector comprises one or more of a power connector, a fluid connector for liquid, a fluid connector for a high pressure air source, a data connector a control connector and an interlink to a pump or a valve of said apparatus. Optionally or alternatively, said module comprises said storage and said mixing chamber.

There is provided in accordance with an exemplary embodiment of the invention, a replacement cartridge for a substance detector comprises:

a mixing chamber;

a container including a reagent; and a fast connector. Optionally, mixing chamber comprises a cyclone.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 13A-13E are engineering drawings of a cyclone design, in accordance with an alternative exemplary embodiment of the invention.

DESCRIPTION OF SPECIFIC EMBODIMENTS OF THE INVENTION

The present invention, in some embodiments thereof, relates to detecting systems, and more particularly, but not exclusively, to a device useful for detecting certain concealed and non-visible substances.

The invention comprises, in some embodiments, a substance detector capable of detecting the presence of certain substances in an air or swab sample. The substance detector comprises a cyclone separator that draws in external air causing the air to spin in a vortex, and a fluid port that sprays a fluid into air, before and/or after it forms a vortex. In an exemplary embodiment of the invention, the fluid attracts (e.g., adsorb and/or dissolve) and/or engages in a chemical reaction with substances that may be present, and/or directs the substances to an output port where the chemical change is detected by a sensor. In an exemplary embodiment of the invention, the fluid is thrown by the vortex against a wall of the cyclone and is carried, e.g., by gravity or suction, to a detection area.

In an exemplary embodiment of the invention, the fluid port is optionally optimized so that the fluid spray that emanates from the port enhances the speed and/or efficiency with which the substances move through the cyclone. The optimizations to the fluid spray optionally comprise one or more of cyclone properties (e.g., a particular size, angle, or slot of entry or length of cyclone body or cyclone angle or fluid barrier/damper) and fluid properties (e.g., type, particle size). The fluid is optionally water, a solvent that dissolves the substances and/or a reagent. Optionally there is more than one fluid port, with one port emitting a spray of water or solvent, and another fluid port injecting, spraying, or dripping a reagent, for example, to coat at least part of an inside wall of the cyclone.

In an exemplary embodiment of the invention, the properties are chosen so as to control the reaction time between the reagent(s) and the input. For example, ensuring sufficient and/or not overlong reaction time between reagent admixtures and/or before detection. In an exemplary embodiment of the invention, the properties are modified according to the reagents and/or detection method used.

In some embodiments of the invention, there is at least one reagent input port that injects at least one reagent into the cyclone. The reagent engages in a chemical reaction with substances present in the air sample, and the chemical change is detected by a sensor. Optionally there are two reagent input ports, optionally spaced apart, in the cyclone. Optionally one reagent input port is in an upper part of the cyclone and another is in a lower part of the cyclone.

In an exemplary embodiment of the invention, the chemical change is a change in the color of the substances, and the sensor is an optical sensor sensitive to the RGB components of visible light.

In some embodiments of the invention there is provided an apparatus that separates substances in an air sample. The substance separator comprises a cyclone and a damper configured to guide the substances (e.g., fluid droplets) inside the cyclone towards an output port. Optionally the damper is located along a path of exit of the air inside the cyclone. In an exemplary embodiment of the invention, the damper serves to separate a region with high speed cyclone, which functions to throw droplets against the apparatus wall or other fluid trap and a low speed/low flow area where there is less airflow. Optionally or alternatively, the damper sits on an outflow from the low speed area to trap droplets carried away by the outflow.

In some embodiments of the invention there is provided a substance detector comprising a cyclone and a solid reagent such as a catalyzer or other solid agent which contributes to the detection chemical reaction. Optionally, the solid reagent is located at an output port and is positioned to chemically react or support reaction with the substances. Optionally or alternatively, the solid reagent is located upstream of the detector, for example, in the cyclone body, so that droplets traveling along the cyclone wall contact the reagent. A sensor detects the chemical change. Optionally there is also a reagent input port and a reagent that participates in the chemical reaction with the substance and the solid reagent. Optionally the solid reagent is a metal rod, optionally zinc. Optionally there is a mechanism that advances the rod as a contact tip of the solid reagent is removed by the chemical reactions.

In some embodiments of the invention there is provided a substance detector comprising a cyclone separator and a fluid port that injects a fluid into the cyclone. The fluid port is configured to inject a fluid into the cyclone so that the travel time of the substances within the cyclone falls within a predetermined range. Optionally the configuration of the fluid port comprises any one or more of a size, angle, and slot construction of the fluid port. In an exemplary embodiment of the invention, the range is selected for one or more of:

(a) ensuring that the samples finish reacting with a first reagent before meeting a second reagent, or otherwise to allow a more useful interaction and/or less negative interaction between the reagents;

(b) ensuring that the samples finish reacting with a first reagent before being detected, or otherwise ensure that the samples are detected during a useful detection window thereof;

(c) ensuring that the samples do not decay after reaction and before detection; and (d) ensuring that the samples travel at a desired variability of travel time, for example, enhancing uniformity or encouraging a certain level of variability.

Figure 1:
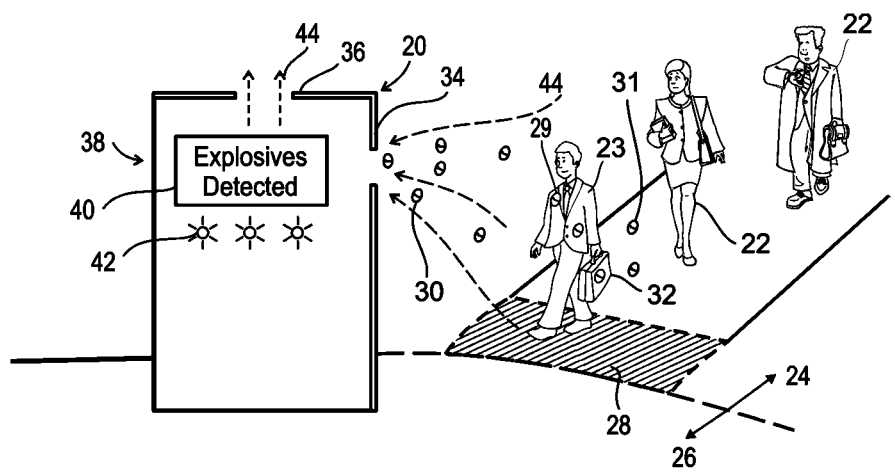
FIG. 1 is a schematic view of a substance detector in use scanning a group of people for the presence of explosives and narcotics, in accordance with an exemplary embodiment of the invention.

In some embodiments of the invention there is provided a method of detecting substances in an air sample. The method comprises applying a centrifugal force to the air sample, spraying a fluid into the air sample, collecting the substances, and detecting a chemical change in at least one of the substances and the fluid. Optionally, the fluid dissolves the substances.

In some embodiments of the invention there is provided a method of detecting substances in an air sample. The method comprises applying a centrifugal force to the air sample using a cyclone separator, providing at least one reagent in the cyclone, obtaining a chemical reaction between the at least one reagent and the substances, collecting the reacted reagents, and detecting a chemical change in at least one of the substances and the at least one reagent. Optionally a first reagent is provided at a first position in the cyclone and a second reagent is provided at a second position in the cyclone.

Before explaining at least one embodiment of the invention in detail, it is to be understood that the invention is not necessarily limited in its application to the details of and the arrangement of the components and/or methods set forth in the following description and/or illustrated in the drawings and/or the Examples. The invention is capable of other embodiments or of being practiced or carried out in various ways.

1. Overview

Referring now to the drawings, FIGS. 1 and 2 show a substance detector 20, in accordance with an embodiment of the invention.

In FIG. 1 substance detector 20 is shown in the context of an exemplary security application in which individuals or persons 22 are checked to detect the presence of explosives, narcotics, or other harmful or illegal materials. The scene in FIG. 1 could be any location where groups of people gather that might attract malicious activity by terrorists or criminals or serve as a checkpoint therefor, such as an airport boarding gate, office building entrance, shopping mall, subway station, or school. Detector 20 may also be used for processing cargo, such as mail or luggage. Individuals 22 must pass substance detector 20 in order to go from an outside or public area 24 to a secure area 26, such as, for example, from a public street to the inside of a government building. In the exemplary situation as shown, individuals 22 stand in line and proceed, one at a time, to a designated spot or area 28. For convenient reference, the person currently standing in area 28 may be designated as person 23.

In the example of FIG. 1, person 23 is carrying concealed explosives or has recently handled explosives. A property of many types of explosives, such as plastic explosives, and of some other types of contraband is that the material to be detected is often inherently sticky. Handling and packing of the explosives accordingly imparts sticky particulate residues or solid particles 29 to the person's hands. The residues are often sufficiently sticky that traces remain on the person's hands even after repeated washing. The particulate residues then transfer and stick to surfaces subsequently touched by person 23, such as his or her face, hair, and skin, clothing, bag, purse, or briefcase 32, car door handle, and other items. In addition to small solid particles 29, traces of the explosives may also be present or be given off in the form of a gas, such as vapor or aerosol 31. Some of the gaseous vapor 31, will float or be suspended in the ambient air around person 23. Alternatively, like solid particle residue 29, some of the vapor 31 will settle on or adsorb to the person's skin, hair, and garment fibers.

The presence of minute particles 29 and vapors 31 on the person's body, possessions, and/or surrounding air provide an avenue for detection of the presence of explosives and other contraband. To the authorities, the detection of even trace residues of critical substances on a person raises a distinct possibility of illicit activity, and may provide sufficient justification to warrant further and more personal investigation such as inspection of the person's luggage.

For convenient reference, the various forms of detectable material such as particulate residue and solid particles 29, and gaseous vapor, molecules, and aerosols 31, may collectively be designated as substances of interest (or just "substances") 30. In the figures, substances 30, whether particles 29 or vapors 31, are represented as bisected circles. It is noted however, that the activity of detector 20 may be different for different phase properties of the substances.

In FIG. 1 substance detector 20 is shown as a "black box" having an air inlet 34, an air outlet 36, and an optional user interface 38. User interface 38 may be used to communicate with an operator (not shown) of substance detector 20, and may include, for example, one or more display screens, status lights or LED, indicators, audible recordings or alarms. In the figure, user interface 38 is shown as comprising a display screen 40 and three status lights or LEDs 42.

In an exemplary embodiment of the invention, substance detector 20 is designed to collect and analyse both trace particles 29 and vapors 31. In operation, a vacuum created inside substance detector 20 (optionally by ejecting air in a flow, passing an air flow past an output of detector 20 or by other means known in the art) creates a strong suction force at air inlet 34. As shown in FIG. 1, the suction draws air or airstream 44, primarily from person 23 and the ambient environment around designated area 28, to flow into substance detector 20 through air inlet 34. In this way, some of the explosive particles 29 and vapors 31 that are resting on person 23 and/or suspended in the air around person 23 will be drawn into substance detector 20. In addition to receiving substances 30 by air suction, further samples may optionally also be taken by having an operator (not shown) swab the body, clothing, and/or bag 32 of person 23 directly. In some embodiments the swabbing is done with a particle collector 37 (FIG. 3) that applies suction to the surface being wiped. The particles or substances 30 are collected onto a pre-concentrator (not shown) and then desorbed into the substance detector. Optionally or alternatively, such a sample is swabbed and then held near an inlet of device 20.

As discussed in greater detail below, substance detector 20 separates and collects substances 30 that enter the device, identifies them as being substances or materials of concern, and alerts the attending authorities. In the device of FIG. 1 alerts are optionally performed by displaying the message "Explosives Detected" on display screen 40 and/or by activating status lights 42. Other types of alerts may include, for example, activating an audible alarm, or sending an electronic signal to police or other authorities elsewhere in the building or at a remote location.

Figure 2:
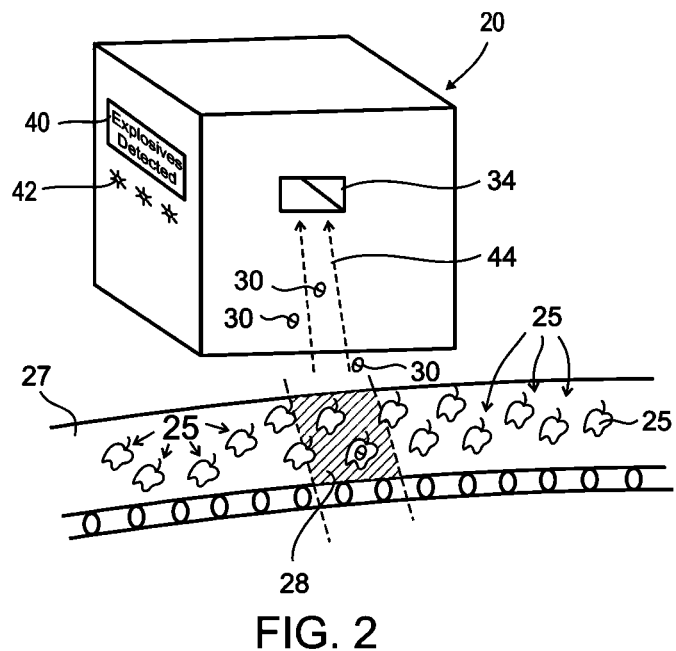
FIG. 2 is a schematic view of the substance detector of FIG. 1 in use scanning a food production line for the presence of pesticides, in accordance with an exemplary embodiment of the invention.

FIG. 2 is an exemplary non-security application, the inspection of produce for the presence of pesticides. As shown, food produce 25 moves on an automated conveyor belt 27 past substance detector 20, with air optionally blowing on the food. Designated spot 28 in this case is a section of conveyor belt 27 immediately adjacent to air inlet 34. Upon detection of a predetermined threshold level of pesticides, an alarm or alert is activated. In this example a human operator may not need to be present at all times, so the alert may, for example, summon an attendant or stop movement of the conveyor belt.

Figure 3:
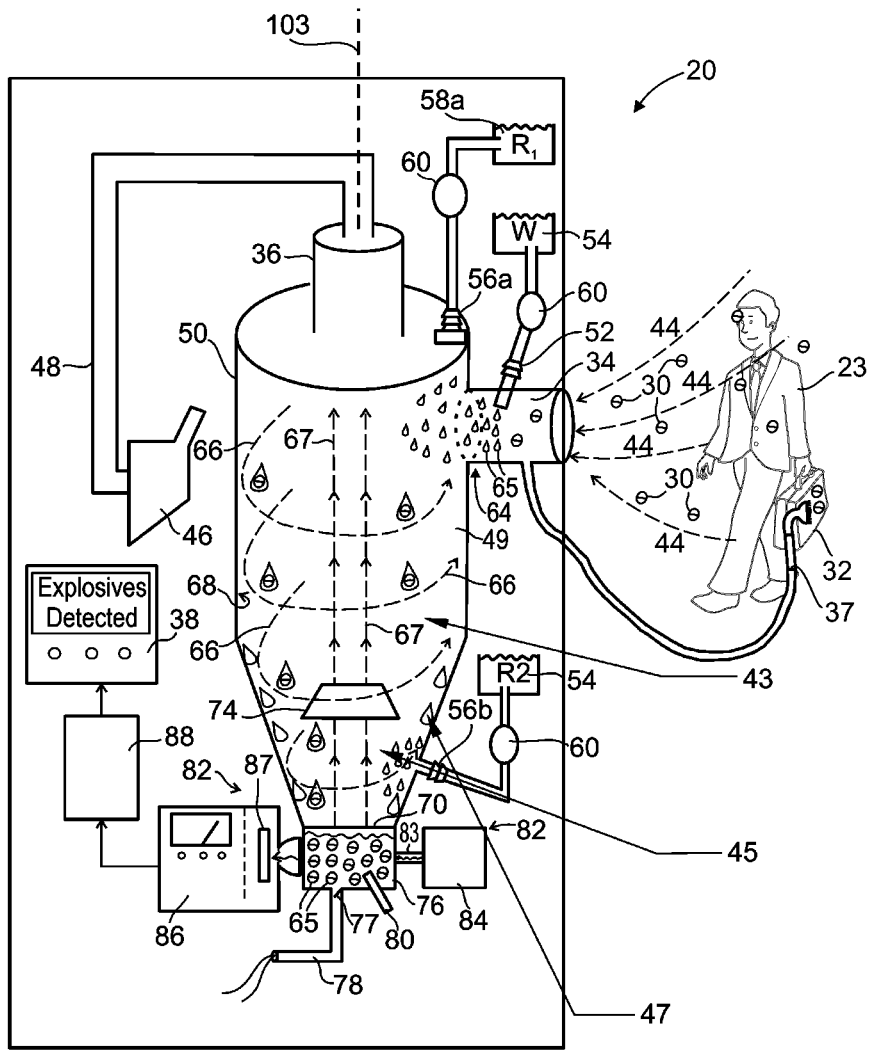
FIG. 3 is a schematic view of the substance detector of FIG. 1, showing some of the detector's component elements, in accordance with an embodiment of the invention.

FIG. 3 is a schematic view showing some of the component elements of substance detector 20, according to an embodiment of the invention. An air compressor 46 acting through connecting tubing 48 pumps air from an interior 49 of a cyclone separator 50 (also called "cyclone"), which is connected to air inlet 34. The removal of air creates a vacuum inside cyclone 50, which in turn creates the suction that pulls air 44 into cyclone 50 through air inlet 34, as described above. In some embodiments a compressed gas bottle or a vacuum flask may be used to create the vacuum instead of air compressor 46. The strength of the vacuum may be varied according to the application. In some embodiments, a vacuum sufficiently strong to create a flow rate of air 44 of 1000 liters/minute has been found to be adequate. In addition to substances 30 pulled into cyclone 50 by the flow of airstream 44, FIG. 3 also shows particle collector 37 in use capturing substances 30 by swabbing bag 32 held by person 23.

Cyclone 50 in some embodiments includes a fluid inlet or nozzle 52 which delivers a fluid (optionally as a spray) such as water or solvent from a receptacle 54, and one or optionally two or more (two shown) reagent inlets 56a and 56b, which deliver reagents $R_1$ and $R_2$ into cyclone 50 from receptacles 58a and 58b, respectively. Reagent inlet 56a is optionally at an entrance to cyclone 50, where cyclone 50 meets air inlet 34, and reagent inlet 56b is optionally at a lower part of cyclone 50. One or more hydraulic devices or pumps 60 are used to pump the fluids and reagents from their receptacles to cyclone 50. Optionally, the fluid provided by fluid inlet 52 is in the form of a fluid spray 64 comprising small droplets 65. Individual particles 29, vapors 31, and other substances, celyollectiv 30, that are brought into cyclone 50 with air 44 tend to be captured by droplets 65, thus possibly assisting in their extraction/concentration.

Inside cyclone 50, the structure of the cyclone causes airstream 44 to rotate in a rapid spiral or vortex 66, shown as dashed lines in FIG. 3, at an upper section 43. Vortex 66 creates a centrifugal force that swings droplets 65 outwards, into contact with an inner wall 68 of cyclone 50. Upon hitting the wall droplets 65 lose momentum (shown as 47) and fall out of cyclone 50 at its bottom through a substance outlet 70. In general, the lower section of the cyclone, indicated here as 45, has significantly lower airflow, and possibly no cyclonic activity. Optionally or alternatively, as the rotating flow moves towards the narrow end of the conical lower section, the rotational radius of the stream is reduced, forcing the airstream into a smaller diameter spiral. This forces smaller and smaller diameter particles or droplets against the sides of the container, taking them out of the airstream. While the droplets are ejected out the bottom of cyclone 50, a second, inner vortex 67 or airflow carries clean air 44 up and out of the device through air outlet 36. In an exemplary embodiment of the invention, there are two return flows, one which returns flow from the upper section 43, and one which returns from the lower section 45. Optionally, for example as described below, the second return flow is used to aid in the droplets reaching the detector. In some embodiments, there is no second return flow. The damper, described below, may serve for damping one or both flows and/or for distinguishing between the two airflow regions of the cyclone.

In some embodiments of the invention, reagents $R_1$ and/or $R_2$ are fluids delivered as a spray. In interior 49 of cyclone 50 the reagents are drawn and become attached to water droplets 65, and consequently come into contact with substances 30. In an exemplary embodiment of the invention, the reagents are selected to have a chemical profile that will react with the specific substance(s) 30 being detected. For example, in the exemplary application of FIG. 1, reagents $R_1$ and $R_2$ are selected that react with explosive or narcotic particles and gases, and in the exemplary application of FIG. 2 reagents are selected that react with pesticides. Different types of chemical reactions may take place in different embodiments of the invention. In some embodiments the chemical reaction comprises a change in color of the particles 30 and/or of the reagent itself. For convenient reference, in FIG. 3 substances 30 that have experienced a chemical reaction are shown as bisected circles with a gray-scale shading.

An optional damper 74 blocks droplets 65 that rise with air 44 and redirects them so that they drip down and fall out of substance outlet 70. As noted above the damper can be, for example, wings that extend into the flow (e.g., for top, fast cyclone section) and/or a wire mesh, for example, which intersects with the flow (e.g., for lower, slow flow, section). A collector 76 is positioned at substance outlet 70 to collect deposited droplets 65. Methods other than gravity may be used to guide the movement of droplets. A liquid outlet or discharge port or tube 78 is connected to collector 76, to remove droplets 65 after they have been analyzed, as discussed below. An optional catalyzer or solid reagent 80 may be placed in or close to collector 76. In an exemplary embodiment of the invention, solid reagent 80 is made of a material that catalyzes or reacts with particles 30 and/or one or more reagents. In some embodiments solid reagent 80 is a zinc rod.

In this way, as shown in FIG. 3, particles and vapors 30 that were initially entrained within air 44 become separated from air 44, and gather and concentrate in collector 76. Since substances 30 in collector 76 have reacted with the reagents inside cyclone 50 and/or with solid reagent 80, they are shown shaded in the figure.

Substance detector 20 optionally further includes a reaction sensing mechanism 82, which is an element or group of elements that senses the presence of substances 30 in collector 76 that have experienced a chemical reaction. In embodiments of the invention in which the chemical reaction produces a change in color, reaction sensing mechanism 82 may conveniently also be referred to as optical or color sensing mechanism 82. In the embodiment of FIG. 3, optical sensing mechanism 82 comprises a light source 84 and an optical or color measuring instrument, or spectrometer 86. Light source 84 illuminates liquid droplets 65 in collector 76, so that substances 30 in the droplets can be viewed by spectrometer 86.

In an exemplary embodiment of the invention, spectrometer 86 includes an optical sensor 87. In some embodiments of the invention optical sensor 87 is specially configured to be particularly responsive and sensitive to changes in color induced in substances 30 by their reaction with the reagents.

Spectrometer 86 optionally includes or is coupled to a device with software specially configured to interpret the color measurements taken by optical sensor 87. Additional exemplary sensors which may be used, include, optical density sensors, polarization sensors, conductivity sensors, TDS sensors, florescence sensors, scattering detectors, specific density sensors and/or sensors for detecting non-dissolving materials.

As shown in FIG. 3, spectrometer 86 communicates with an optional controller 88, which processes the measured reaction or color data and activates user interface 38 as appropriate. For example, if explosives have been detected, an alarm, display screen message, status light, or other form of notification will be activated to alert the operator. If explosives have not been detected, a message may be displayed that person 23 may leave designated area 28 and proceed into secure area 26, and that the next person 22 may now enter designated area 28.

2. Cyclone Separator
(i) Overview

The use of cyclone 50 as a component of substance detector 20, in an embodiment of the invention, was discussed in the section above.

More generally, a cyclone is a device that uses the principle of centrifugal motion to remove particulates from an air, gas, or water stream, without the use of filters. For example, a cyclone may be used in a factory or a mine to reduce the concentration of dust and particles in the air, to make the environment safe for workers. As indicated in FIG. 3, the basic shape of a cyclone is a cylindrical upper section and a frusto-conical lower section. The airstream to be cleaned enters through an air inlet connected at the top of the upper section. Other cyclone designs may be used as well, for example, a flat spiral with one or more tubes or channels for droplet travel. In an exemplary embodiment of the invention, the cyclone includes a section with less flow and to which droplets that attach to the walls or other droplet collector are guided, for example, the lower cone section, for example, being guided by gravity or by slower airflow.

A wet cyclone is, generally, a variation of a standard cyclone in which a liquid aerosol or droplet spray is injected into the airstream as it enters the cyclone. As discussed previously, in an exemplary embodiment of the invention, the aerosol droplets capture the particles and noxious vapors in the airstream, and thereby enhance the efficiency of the cyclone in cleaning the airstream. The liquid from the droplet spray is collected at the bottom of the cyclone in a drain tube. Optionally or alternatively, the droplets start the reacting between the substance(s) and one or more reagents, before collection of the drops. In some embodiments a dust of adsorbing and/or reacting particles is distributed into the air stream instead of or in addition to a mist of droplets.

In some embodiments of the invention, cyclone 50 may be a standard wet cyclone of the type used in industry (or a variation thereof) and other applications to remove particulates from an airstream. In these embodiments the liquid aerosol or droplet spray optionally comprises or includes at least one reagent. Accordingly, in some embodiments and unlike the embodiment shown in FIG. 3, the reagent or reagents would be injected from fluid inlet 52 in air inlet 34, rather than from an inlet located inside cyclone interior 49.

Figure 4:
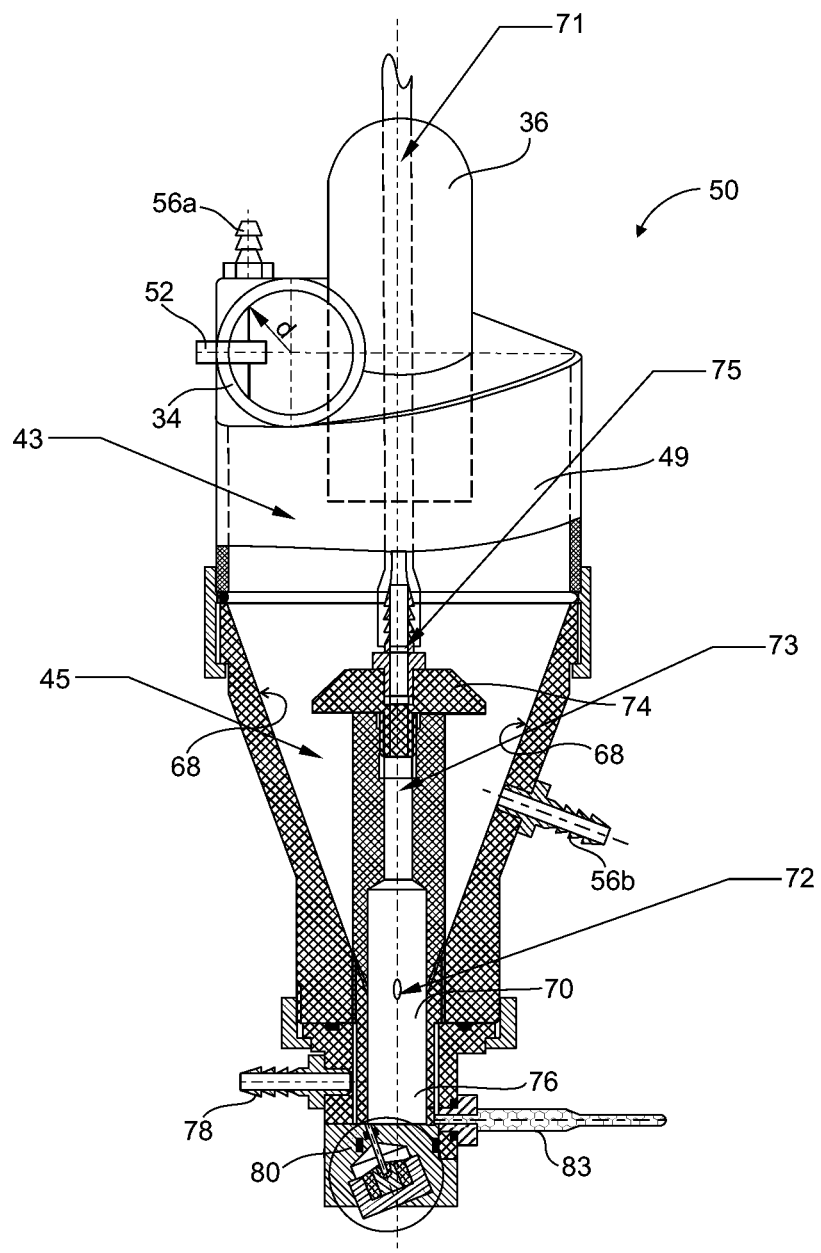
FIG. 4 is a cross-section view of a cyclone separator of the substance detector of FIG. 1, in accordance with an embodiment of the invention.

Alternatively, in some embodiments of the invention cyclone 50 comprises a standard wet cyclone that has been modified to include any one or combination of enhancements discovered by the inventors. Exemplary such enhancements were shown in the embodiment of FIG. 3, and are also shown in FIG. 4 in a more detailed cross-sectional view of cyclone 50. As indicated in FIG. 4, cyclone 50 may include improved fluid inlet 52, reagent inlets 56, damper 74, collector 76, and/or solid reagent 80. Each of these features is discussed in greater detail below.

In an exemplary embodiment of the invention, cyclone 50 includes an upper section 43 with high air flow and vented by a outlet 36. Optionally, damper 74 (described below) interferes with the exit of droplets. Most droplets may be expected to be thrown against and adhere to the walls of cyclone 50. A lower section 45 may also have some air flow, by air passing through apertures 72 (optionally urging droplets into a collector 76 thereby), and along a channel shown as 73, exhausting via an optional tube 71. Low pressure at tube 71 is optionally caused by nearby or surrounding flow through outlet 36. Optionally, damper 74 includes a filter area 75 which collects droplets. Optionally or alternatively, filter area 75 also collects droplets from air arriving directly from upper section 43. Optionally, the air flow volume and/or speed in section 45 is less than 50%, 20%, 10% or intermediate values of the airflow in section 43. In an exemplary embodiment of the invention, gravity causes droplets that adhere to the wall to travel until apertures 72 where they enter collector 76 and reach a detector, as described below, for example.

(ii) Fluid Inlet/Nozzle

A top view of an upper section of cyclone 50 is shown in FIG. 5. In this figure it can be seen that an atomizer 90 is positioned inside air inlet 34. Atomizer 90 creates and injects fluid or liquid spray 64 into cyclone 50. Fluid inlet or nozzle 52, which was described above, is the outlet of atomizer 90 through which spray 64 is delivered.

As indicated in the figure, atomizer 90 comprises a pressurized air input 92 and a fluid input 94. Pressurized air from air input 92 flows in an internal channel 96 and mixes with fluid flowing in an internal channel 98 just before the entry to nozzle 52. The result of the mixing is fluid spray 64, which emanates from nozzle 52 into air inlet 34. Fluid spray 64 is an aerosol mist comprised of fine droplets 65. In some embodiments, fluid spray 64 is continuous. Atomizer 90 is capable of precise application of fluid in very small doses.

As shown, fluid inlet 52 is positioned close to an entrance 100 to cyclone 50. In addition, air inlet 34 physically narrows as it approaches entrance 100. As a result, as droplets 65 are sprayed from nozzle 52, they form a dense mist that fills the space in front of entrance 100. Airstream 44 is forced to pass through dense aerosol mist 64 in order to enter cyclone 50. Many of substances 30 in airstream 44 are consequently forced into contact with the surface of the liquid droplets. Once contact is made, the particles and vapors adhere or adsorb to the droplet surface. Shortly after adsorption, the particles and vapors may be absorbed into droplets 65 by entering inside the droplets. Optionally or alternatively, the substances are dissolved by the droplets. Optionally or alternatively, such dissolving assists in adsorption.

The efficiency of capture is optionally aided by the high concentration or density of aerosol droplets 65 within the relatively narrow space inside air inlet 34 as it meets entrance 100 and/or by the effective surface area of aerosol droplet 65. In some cases (e.g., for some sets of materials and fluids), once a particle or vapor is captured by adsorbing to the surface of a droplet 65, there is a very good chance that the particle or vapor will subsequently be absorbed into the droplet.

In an exemplary embodiment of the invention, particles 29 and vapors 31 are extremely small and light, and as a result are always at some risk of floating away or otherwise escaping airstream 44. However, when absorbed into droplets 65, the droplets act as liquid "carrier" that impart a much greater mass and volume to the tiny particles and vapors, so that they are easier to handle and be directed by the centrifugal forces to the bottom of the cyclone.

The efficiency of operation of cyclone 50 may be enhanced through adjustment of one or more parameters relating to fluid nozzle 52. Air flow capacity, or the volume of air in airstream 44 that can be accommodated by air inlet 34, may be raised by modifying the size of inlet surface area relative to outlet surface area.

Another potentially useful parameter is inlet velocity, or the speed or flow rate of fluid spray 64 from nozzle 52. This can be varied by increasing the pressure of pressurized air entering pressurized air input 92. In some embodiments, an inlet velocity of 2-4 ml/second has been found to be adequate.

Figure 5:
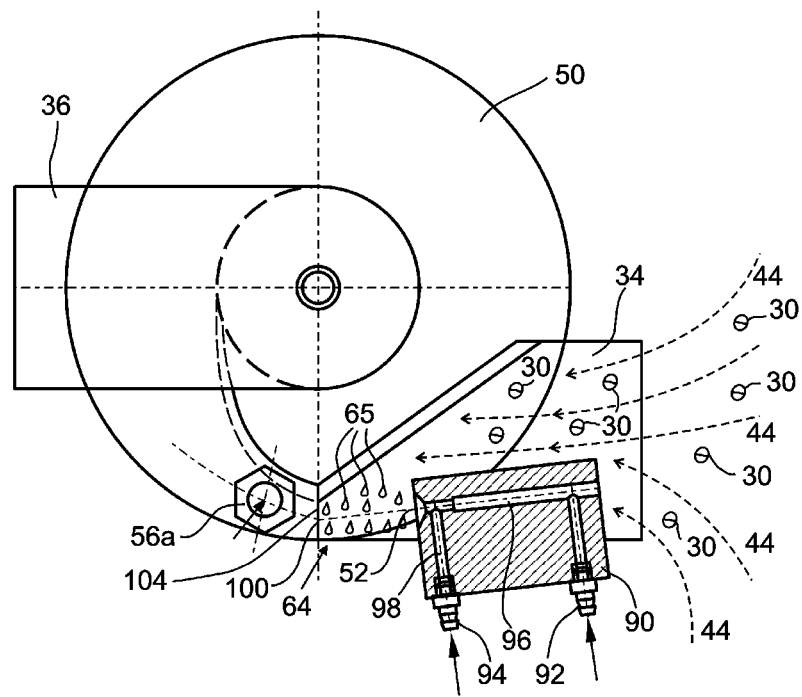
FIG. 5 is a cross-sectional view of an upper part of the cyclone separator of the substance detector of FIG. 1, in accordance with an embodiment of the invention.

The inventors have discovered that, in some embodiments of the invention, adjustment of a nozzle angle 102 relative to cyclone axis 103 (FIGS. 3 and 13B) and use of a slot 104 (FIGS. 5 and 13A) can increase the efficiency at which substances 30 are caught in and/or detected with the aid of spray fluid 64. Another potential benefit is that the time during which substances 30 fall to the bottom of cyclone 50 can be controlled, to be, for example, up to 2 or 4 seconds, up to 900 ms, up to 600 ms, at least 200 ms, at least 400 ms, at least 1000 ms, depending on need. For example, in some embodiments, nozzle angle 102 is in the range of 1-3 degrees relative to the horizon, as shown in FIG. 13B, and slot 104 is positioned as shown in the figure. With these settings, the inventors have observed a range of the time for substances 30 to reach the bottom of the cyclone from about 800 msec to about 1200 msec.

Another parameter is the size of droplets 65. In some embodiments, the efficiency of capture of substances 30 from airstream 44, the percentage of substances 30 that react with reagents, and the speed of substances 30 traveling to the bottom of cyclone 50 are enhanced when droplets 65 are sized in the diameter range of about 0.1 to 8 micron, though other sizes such as less than 0.07 microns, about 3 microns and more than 10 microns, or intermediate or greater diameters can be provided as well. In general, smaller drop sizes provide a more efficient cyclone operation. Optionally, the size of droplets is controlled by one or more of the outlet diameter of nozzle 52, the air pressure of nozzle 52 and the fluid volume, which is transferred into nozzle 52. The size of droplets 65 can be adjusted by modifying the flow of pressurized air and fluid at inputs 92 and 94 of atomizer 90. The efficiency of droplet collection of substances 30 is relatively high, and in some embodiments having settings as described above can be over 98-99%.

In some embodiments water is used as the fluid injected by fluid input 94 and as the basis of droplets 65. In other embodiments a solvent such as acetone may be used. In particular, solvents may be selected that dissolve substances 30. Use of such solvents in some embodiments may improve the efficiency of the chemical reaction with the reagents and the likelihood of making an accurate measurement of the concentration of substances 30.

(iii) Reagents (1) Reagent Selection

In any particular embodiment of substance detector 20, one or more reagents are selected that chemically react with substance(s) of interest 30 to be detected by that embodiment. The type of chemical reaction corresponds with the type of detection being performed. For example, where color detection is performed, the reaction should produce a detectable change in color in substances 30. Accordingly, for each type of substance 30 there is a reagent or combination of reagents that make the detection process accurate and reliable. While the chemical reagents are specific for different substances, use of a single, universal chemical reagent that can detect a range of substances 30 is also comprehended by the present invention.

In addition to sensitivity to the substance to be detected, the selected reagent should also produce the chemical reaction sufficiently fast so that the reaction is completed within the time that the reagent contacts the substance and drops to collector 76 at the bottom of cyclone 50 and/or within a cycle time of the sensing system and/or of an exhaust system thereof.

Other factors for consideration are the concentration and temperature at which each reagent is stored and injected into the cyclone.

Some examples of specific reagents for different types of substances to be detected, such as explosives and narcotics, are provided in Section 6 below.

(2) Reagent Storage and Connection to Cyclone

The reagents selected for use in a particular application of substance detector 20 may be conveniently stored in close proximity to cyclone 50. As shown previously in FIG. 3, in some embodiments reagents are stored in receptacles 58, and connect to reagent inlets 56 by pumps 60.

The pumps create a pressure differential that draws the reagents out of their receptacles and towards reagent inlets 56, from where they are injected into cyclone interior 49. Reagent inlet 56 can be a nozzle, for example, similar to fluid nozzle 52, that injects the reagent in the form of a spray. In some embodiments reagent inlet could deliver the reagent in a form other than a spray, such as by injection or dripping. In some embodiments the reagent may have a non-liquid form, for example as small particles, and reagent inlet 56 could be configured to deliver particles rather than a liquid. In some embodiments it is advantageous to spray the reagents. Spraying converts liquid reagents into tiny droplets, which can increase the efficiency with which the reagents attach and/or are absorbed into both fluid droplets 65 and any isolated particles or vapors 30 that have not been captured by fluid droplets 65.

Other factors which may be considered are the number of reagent inlets 56 and their location in cyclone 50. As noted above, in some embodiments reagents could be dispensed from fluid inlet 52, located in air inlet 34. In other embodiments separate fluid and reagent inlets are used, such as the embodiments shown in FIGS. 3 and 4. Use of more than one reagent inlet can be advantageous because it enables substance detector 20 to detect a wider range of substances 30. However, reagents injected at a particular position in cyclone 50 may be of a type which have to be presented one at a time. Some reagents cannot be mixed because that would lead to mixed color reactions which would not be detectable and/or other failures. Accordingly, when using two or more reagent inlets 56, it may be advantageous to space the reagent inlets as far apart from one another as possible so that there is minimal interference between reactions occurring with different reagents.

In some embodiments, a good location for a reagent inlet is at an entrance to cyclone 50, where airstream 44 enters cyclone interior 49 from air inlet 34. An example of a reagent inlet in this position is reagent inlet 56a in FIGS. 3 and 4. Reagents injected from this location will meet incoming aerosol spray 64 right as it enters the cyclone, which increases the chances that the reagents will attach to droplets 65 or isolated substances 30 and perform the desired chemical reaction. A good location for a second reagent inlet 56b is in a lower part of cyclone 50, as shown in FIGS. 3 and 4. In this way, reagent inlets 56a and 56b will be spaced relatively far apart so as to minimize interference between the reactions from each reagent. In some embodiments, three or more reagent inlets 56 may be used, as long as there is sufficient spacing so that mixed color reactions are not a problem. Optionally or alternatively, mixed reactions are avoided or reduced by controlling travel time of droplets between reagents.

(3) Exemplary Reagent Sequence, Timing, and Flow Rate

For each reagent inlet 56, a selection is made as to how many reagents may be delivered from that inlet. In some embodiments one reagent is delivered. In other embodiments two or more reagents may be delivered sequentially in time. For example, in the embodiments of FIGS. 3 and 4, a predetermined reagent profile may be programmed by which inlet 56a delivers two reagents R1a and R1b, and inlet 56b delivers three reagents, R2a, R2b, and R2c.

When two or more reagents are delivered from a single reagent inlet, the duration of time that each reagent is delivered may be independently specified. For example, in the case above, inlet 56a could deliver reagent R1a for 400-600 msec followed by an optional reagent R1b for 700 msec after a delay of 700 msec, while inlet 56b, after a delay of, for example 200 msec delivers reagent R2a for 500 msec, reagent R2b for 400 msec, and reagent R2c for 600 msec. These are just exemplary numbers, in general, a controller may control, for example, the order of reagent provision, the duration of provision and the delay between provisions of reagents, a delay within a port and a delay between ports. In an exemplary embodiment of the invention, the reagent delivery and detection operation is continuous, once the detection is initiated. Optionally, any and all of the delays may be optional and/or may be different from those shown above. Optionally, a delay is provided between a first nozzle and a second nozzle, to allow time for samples to travel between the nozzles.

Where multiple reagents are emitted from a single reagent inlet 56, separate receptacles 58 are optionally included in order to store each reagent. There may also be provided a capability to connect each receptacle 58 individually to the common reagent inlet 56. Accordingly, in these embodiments substance detector 20 may include a switching mechanism to switch between receptacles so that the desired reagent can be delivered at the appropriate time. In some embodiments a hydraulic switch may be used. Control and activation of the switch may be performed by controller 88.

A factor that possibly affects performance of substance detector 20 is the flow rate or speed at which the reagent is sprayed or delivered from the reagent inlets. The inventors have discovered that efficient (=high sensitivity) operation of substance detector 20 can be encouraged by regulating reagent flow rate in proportion to the flow rate of fluid from fluid inlet 52.

For example, in the embodiment shown in FIGS. 3 and 4 having a fluid inlet 52 spraying water, a reagent inlet 56a spraying a first reagent R1 at an entrance to the cyclone, and a second reagent inlet 56b spraying a second reagent R2 at the bottom of the cyclone, the following flow rates produced adequate results:

| | |
|---|---|
| Fluid inlet - water injection rate: | 2.0-3.5 milliliter/minute |
| Reagent 1 injection rate: | 1.5-3.5 milliliter/minute |
| Reagent 2 injection rate: | 1.0-2.5 milliliter/minute |

In embodiments in which a reagent inlet 56 delivers more than one reagent sequentially, the different reagents could be delivered at different flow rates and/or in a manner which provides different droplet sizes for different injections. Optionally or alternatively, a same reagent can be provided at a non-uniform rate and/or with varying (over time) droplet sizes. Accordingly, while aerosol spray 64 is produced continuously, the reagent spray may be changed according to a pre-determined reagent profile.

Sequential cycling of reagents at incorrect timings may affect the efficiency of substance detector 20, because the right reagent might not be present in the droplet at the time that a particular explosive is sampled. This may reduce the detection rate of substance detector 20.

(iv) Damper

In some embodiments, it is desired that as many particles and vapors 30 as possible should be captured and delivered to collector 76 where they can be detected by spectrometer 86, for example, for efficient operation of detector 20. In some systems, however, a small percentage of substances 30, whether isolated or absorbed in droplets 65, will fall into inner vortex 67 and exit cyclone 50 through air outlet 36. These substances, if allowed to escape, will not be detected by the system and represent a net loss of efficiency.

As noted, damper 74 is optionally placed in the air exit path of the inner air spiral. In that position stray substances 30 that were on the path to air outlet 36 will instead collide with or otherwise be attracted to damper 74, or possibly be thrown against the wall or a different droplet collector, such as a mesh. Upon contact, many of substances 30 will adhere to the surface of damper 74, and subsequently drip off under the force of gravity and fall into collector 76 where they join the bulk of substances 30 already captured. While substances 30 are blocked, damper 74 is configured to allow air 44 to pass through to air outlet 36. In this way, the percentage of substances 30 that are captured increases and the efficiency of the system improves. In some embodiments, optional damper 74 enables collection of approximately 99% of substances 30 that enter air inlet 34.

In some embodiments, damper 74 is made of a material to which the droplets are expected to be attracted. Optionally, the damper is electro-statically charged or is configured to generate such a charge for itself. Air 44 in vortex 67 is able to pass through damper 74, for example, via channels 73 and/or by damper 74 being apertured, for example, in the form of a net or a mesh. Other configurations of damper 74 are also comprehended by the invention, and may be optionally used in some embodiments.

In an exemplary embodiment of the invention, damper 74 may be moved along an axis of the cyclone and/or otherwise, for example, to control the air flow in different parts of the cyclone. In an exemplary embodiment of the invention, the position of the damper relative to the second reagent inlet port is controlled to have a desired effect on time and/or probability for droplets to reach the second reagent.

(v) Collector

Collector 76 may be any container that can hold a liquid formed by the collection of droplets 65. Collector 76 may be viewed as an add-on or adapted bottom of cyclone 50, as in some embodiments it attaches directly to the bottom of cyclone 50. In an exemplary embodiment of the invention, collector 76 is designed to have a desired volume. Optionally or alternatively, the collector is designed so as to include a cavity lower than a detector and/or a solid reagent thereof. This may allow for a minimum of material to be collected before being detected. In an exemplary embodiment of the invention, the detector is positioned above the solid reagent, to ensure reaction therewith before detection.

In an exemplary embodiment of the invention, the outlet (described below) is positioned so that a minimum amount of material remains in the collector.

In an exemplary embodiment of the invention, the detector can detect once about 1 ml of fluid is collected. Optionally, the solid reagent is positioned just above the detector or to its side, e.g., if the reagent and detector are in same chamber. Otherwise, the reagent is optionally lower than or at same height as outlet which leads to detector.

When used in a system that performs color detection, collector 76 optionally has a glass or transparent surface or window to enable the fluid to be viewed by spectrometer 86. Optionally, collector 76 is a glass tube.

In an exemplary embodiment of the invention, collector 76 includes a discharge valve 77 or other means (e.g., a pump or gravity fed outlet or collection vial or absorbent material) to enable the fluid in collector 76 to be discharged through liquid output port 78 once detection of the current fluid contents has been completed. Optionally, discharge valve 77 is closed while collector 76 accumulates fluid, and opens when detection is complete and collector 76 is ready to receive fluid for the next detection.

In some embodiments, substance detector 20 is configured so that detection is performed by spectrometer 86 when collector 76 receives a predetermined volume of liquid. When a sensor (not shown) senses that this volume has been reached, discharge valve 77 is opened for a specified time to allow the contents of collector 76 to flow out, whereupon discharge valve 77 is then closed. In some embodiments of the invention, the volume of collector 76 is 2-3 ml. In some embodiments, the rate at which fluid droplets 65 flow into collector 76 is about 1-4 cm/s.

Collector 76 is positioned at substance outlet 70 at the base of cyclone 50. It is advantageous to provide a sealed connection between substance outlet 70 and an upper rim or lip of collector 76, so that substances 30 passing through substance outlet 70 cannot escape, and so that ambient particles or vapors do not drift into collector 76.

(vi) Solid Reagent

In some embodiments of the invention, solid reagent 80 is included to provide a further opportunity to obtain a chemical reaction and/or ensure reaction and/or enhance a reaction with some substances 30. As shown in FIG. 3, solid reagent 80 is positioned at least partly inside collector 76, so that contact is made between fluid droplets 65 and at least an edge or section of solid reagent 80. In an exemplary embodiment of the invention, solid reagent 80 is a solid material that chemically reacts with one or more of substances 30 to be detected. Solid reagent 80 can be configured in various forms or shapes. In some embodiments solid reagent 80 is in the shape of a rod, and is made of zinc or platinum. Solid reagent 80 is optionally heated (e.g., using an electrical resistance contact heater) to enhance the chemical reaction. In alternative embodiments, solid reagent 80 is in the form of a ring or large particles. Multiple units and/or types of solid reagents may be provided. Optionally or alternatively, the solid reagents are replaced by materials that act as reagents.

Figure 6:
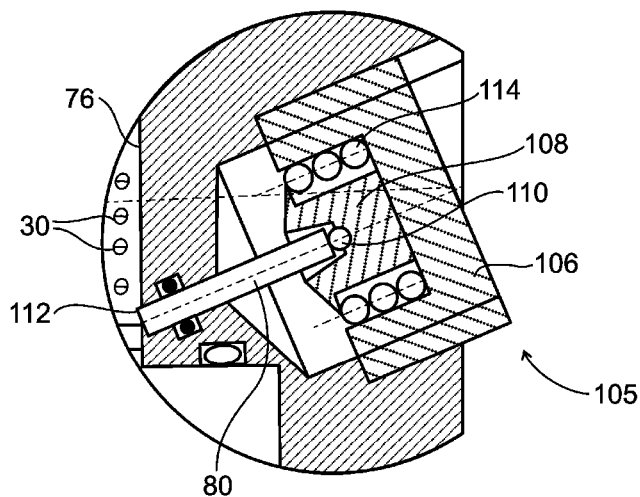
FIG. 6 is a cross-sectional view of a lower part of the cyclone separator of the substance detector of FIG. 1, showing a solid reagent, in accordance with an embodiment of the invention.

FIG. 6 shows a detailed view of an exemplary embodiment of solid reagent 80 in the form of a zinc rod. It can be seen that the rod is supported and held in place by a support mechanism 105 that comprises, for example, a cork base 106 and a bush 108. The bottom of solid reagent 80 rests on a ball bearing 110 that sits on top of bush 108. An opposing tip or edge 112 of the rod is inside collector 76 and in contact with the fluid comprised of droplets 65. Tip 112 is the part of solid reagent 80 that chemically reacts with substances 30 inside collector 76. Tip 112 may gradually become worn down and reduced in size over time as it participates in a series of chemical reactions. In order to ensure that tip 112 is always in contact with droplets 65 inside collector 76, support mechanism 105 includes a spring 114 that urges solid reagent 80 towards collector 76. As shown, spring 114 is wedged between cork base 106 and bush 108. Since cork base is fixed in place, spring 114 applies a constant force on bush 108, which pushes solid reagent 80 into collector 76 as tip 112 gets worn down. In this way, solid reagent 80 comprising a zinc or platinum rod will be usable for an extended period in substance detector 20, without need for frequent replacement. In an exemplary embodiment of the invention, the rod includes a groove with a matching pin on the apparatus (or vice versa or other guide and stop mechanism, such as a pin that matches a protrusion or an axially elongate protrusion on the rod) or the tip of the rod is pressed against a stop by the spring, so that as the rod is used up, it can advance. Optionally or alternatively, the rod may be advanced using a timer and motor or other actuator or using a sensor (e.g., which senses if the rod is in contact with liquid, for example, based on electrical resistance) or manually.

Optionally or alternatively, to using a rod, a solid reagent can be provided in other forms, for example, a wire, a coil, a spring, a ring, a mesh (e.g., with a plane parallel to the plane of the collected droplets), a net, a perforated disc or other solid forms. Some forms are easier to feed, while other forms are easier to replace. Optionally, for example a ring, is provided fixedly mounted into the detector or collector.

In some embodiments, the solid reagent is provided before the collector, for example, inside the cyclone or as part of a pathway from the cyclone to the detector.

Optionally, the solid reagent (e.g., a rod), is fed form the bottom. Optionally, however, this and/or other feed positions are avoided if there is a chance of creating bubbles (e.g., due to the reaction) in the field of view of the optical detector.

In an exemplary embodiment of the invention, the height of fluid in the collector (e.g., and contact with solid reagent) is controlled, for example, by the height of the outlet and/or rate of outlet pumping.

An example is provided to illustrate how the inclusion of optional solid reagent 80 may be used to enhance the range of detection of substance detector 20. In some embodiments of the invention, reagent inlet 56a may spray a first reagent R1 to detect a first type of explosive, and reagent inlet 56b may spray a second reagent R2 to detect a second type of explosive. Solid reagent 80 may be selected to enhance a reaction of the reagents with a third type of explosive. In this way, substance detector 20 may be configured to detect three types of explosives, and is accordingly more versatile and useful than a detector that could only detect two types of explosives. In other embodiments, the reagents interact, for example, the second explosive may be detected by the combination of two reagents. In another example, the provision of the first reagent is such (e.g., misting or injection method) that not all the air interacts with it and some air only interacts with the second (or third) reagent.

(vii) Exemplary Substance Flow

Figure 7:
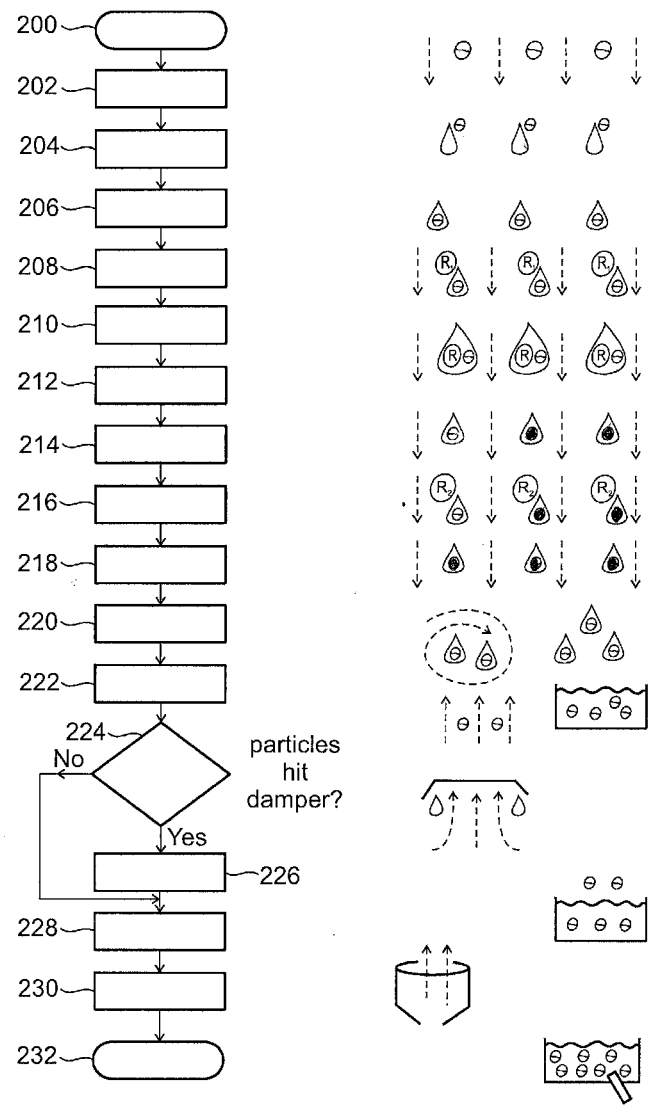
FIG. 7 is a flow chart and graphic illustration of the processes encountered by substances of interest as they flow through the cyclone separator of the substance detector of FIG. 1, in accordance with an embodiment of the invention.

A flow chart summarizing the flow path of particles 30 through substance detector 20, in accordance with an exemplary embodiment of the invention, is shown in FIG. 7. For additional clarity, a graphical illustration of the various processes encountered by particles 30 is also shown.

Upon startup of substance detector 20 (module 200), air compressor 46 is activated (module 202). This creates a vacuum in interior 49 of cyclone 50, and draws airstream 44 containing particles and vapors 30 to be detected into air inlet 34 (module 204). Airstream 44 converges within the narrowing passageway of air inlet 34 and passes through the dense aerosol mist or fluid spray 64 created by pressurizing air and water (or solvent) through fluid nozzle 52 (module 206).

Initially, substances 30 adsorb or attach to the surface of droplets 65. Subsequently, particles 30 may be absorbed and/or dissolved into the interior of droplets 65 (module 208). Airstream 44 proceeds into cyclone 50 from air inlet 34.

Upon passing through the entrance to cyclone 50, airstream 44 passes through reagent spray R1, which adheres to the surface of droplets 65 (module 210). Subsequently, droplets of reagent R1 are absorbed into droplets 65 (module 212), and possibly chemically react with any particles or vapors 30 that are on or inside those droplets (module 214). The chemical reaction is with a first type of substances 30 with which reagent R1 has a chemically appropriate profile. The result of the chemical reaction may be a change in color, for example, red. Substances 30 that are of a different type will not react with reagent R1 and will not change color. In the example shown next to module 214, two substances 30 react with reagent R1 and are shown shaded in color, and one substance 30 does not react with reagent R1 and is shown unshaded.

Airstream 44 rotates in an air spiral or vortex down cyclone 50. At a lower section of cyclone 50, airstream 44 encounters a second reagent spray R2 or droplets contact such a reagent on a wall of the cyclone, where the process of adhesion (module 216), absorption, and chemical reaction (module 218) is repeated. In this case, the chemical reaction is with a second type of particle or vapor 30 than that which occurred in the first reaction and/or a reaction in which both reagents cooperate, for example, by acting together or by one acting on the results of the reaction of the other. The result of this reaction is that substances 30 of the second type change color, for example, to blue. In the example shown next to module 218, the previously unreacted substance 30 has reacted with reagent R2 and is now shown shaded in color.

Continuing within cyclone 50, airstream 44 is optionally continuously, and possibly previously, subject to the centrifugal spin applied by the cyclone, which separates droplets 65 from airstream 44 (module 220). Substances 30 are forced to the outside, collide with the inner walls 68 of cyclone 50 and fall out of substance outlet 70 and into collector 76, while airstream 44 gathers into second, inner vortex 67 and flows upward (module 222). As shown in the accompanying illustration, some stray droplets 65 containing reacted substances 30 remain in airstream 44. In an exemplary embodiment of the invention, the duration of the cyclonic movement of the drops is selected to assist in increasing adhesion of the sample to the drops and/or adhesion of the drops to the cyclone wall. In some embodiments, mixing is efficient enough without cyclonic action and the spraying of mist onto the air intake and then separation is without a cyclone, but rather, for example, along an elongate flow channel with an optional droplet trap, such as a charged net.

As the inner spiral of airstream 44 rises it passes through damper 74. Stray droplets 65 collide with damper 74 (module 224), adhere to its surface and fall off and into collector 76 (module 226). Airstream 44 continues upwards and exits cyclone 50 at air outlet 36 (module 228). The fluid comprising collected droplets 65 in collector 76 experiences a third chemical reaction inside collector 76, in this case with solid reagent 80 (module 230). This reaction will affect a third type of substance 30 and change its color, for example, to green. Substances 30 of the first and second type will not be negatively affected by solid reagent 80. Substances 30 in the liquid in collector 76 are now ready for detection by spectrometer 86 (module 232). It should be noted that in some cases it is the reagents that change color and not the substances themselves or a complex of the substances and the reagent.

It may be noted that not all substances 30 are captured by droplets 65. Some particles and vapors 30 that enter cyclone 50 remain isolated and spin with airstream 44 without being part of larger droplet 65. These particles 30 still collide with inner walls 68 of cyclone 50, where they will most likely be captured by liquid droplets 65 streaming down wall 68. During this passage and/or once inside the collector, some of these particles and vapors 30 will encounter one or more of the reagents, including in some cases the reagent with which they react.

Accordingly, there is a good chance that uncaptured particles and vapors 30 entrained in airstream 44 will be detected. Optionally, the exhausted air (or other carrier gas) is reused. Optionally or alternatively, any reagents in the exhausted air are recycled. Optionally or alternatively, the exhaust air is filtered and/or captured, to prevent contamination of the environment, for example, filtered by activated charcoal and/or captured into a compressed gas cylinder.

3. Exemplary optical (Color) Sensing Mechanism

As noted above, optical or color sensing mechanism is an embodiment of reaction sensing mechanism 82 in which the reaction being sensed is a change in color. Optical sensing mechanism 82 accordingly identifies color changes in the event of color reactions resulting from the presence of substances 30 in collector 76, and can be used to detect any material for which there is a suitable colorimetric reagent. Optical sensing mechanism 82 is specially configured to operate in a dynamic environment, e.g., one in which the material being sensed is in constant flow.

Figure 8:
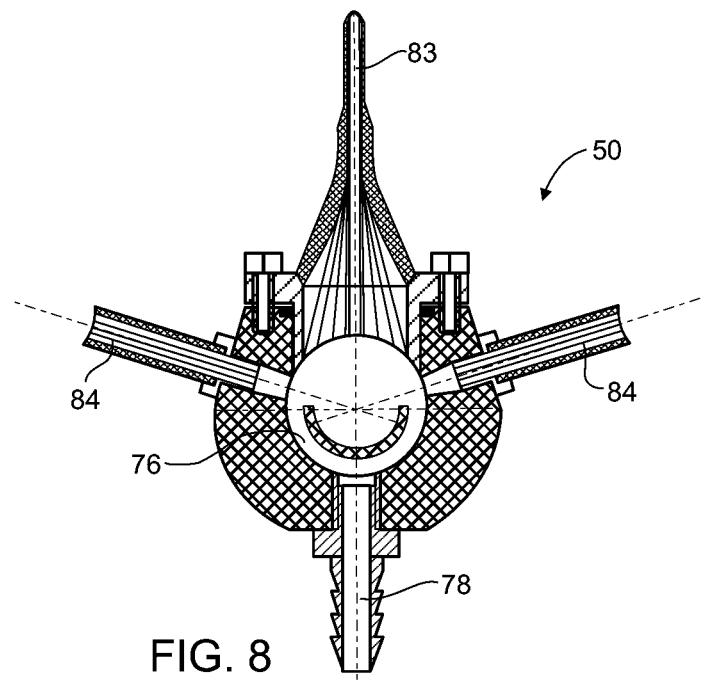
FIG. 8 is a cross-sectional view of a lower part of the cyclone separator of the substance detector of FIG. 1, in accordance with an embodiment of the invention.

The schematic drawing of FIG. 8 shows the elements of optical sensing mechanism 82 according to some embodiments of the invention, i.e. light source 84, optical fiber 83, optical or color measuring instrument 86, and optical sensor 87. FIG. 8 shows some of these elements in a bottom view of cyclone 50.

Light source 84 in some embodiments is an LED laser or diode light delivered through optical fiber 83. The light is optionally directed at the liquid in collector 76 at a defined angle.

In an exemplary embodiment of the invention, optical sensor 87 is a special colorization sensor prepared by the inventors to detect color changes. In some embodiments, sensor 87 measures light intensity in three areas —red 630-670, blue 420- 475, and green 490-610 nanometers (e.g., and may be in the form of a color imaging or linear detector). In other embodiments, one or more wavelength specific sensors are used. Optionally or alternatively, refraction sensors are used, by controlling an angle between the light path and a detector. A potential advantage of an imaging or linear detector is that light absorption can be measured over a greater area of space, for example, along a tube of material, optionally without optics such as lens for light focusing or distribution for the detector (but optionally with optics for the light source, which alternatively may be a leaky light pipe).

Optionally or alternatively, the rate of color change is taken into account while detecting.

In an exemplary embodiment of the invention, an initial reading is taken as a baseline before any contaminated air is provided and/or without reagents. Optionally, the reading is interpreted according to the baseline and/or according to the number and/or amount of reagents used. In an exemplary embodiment of the invention, such an initial reading or other calibration is used to calibrate a range of possible intensities which may be detected by the sensor. In an exemplary embodiment of the invention, a plurality of the detector signals are used for detection by comparison to the baseline settings, even if the expected color change is only in one sensor (e.g., red).

Optionally, measuring instrument 86 is a device that houses optical sensor 87 and that optionally provides electronic circuitry to receive sensor 87 readings and process, display, and/or communicate the information to an operator or to controller 88. In some embodiments detector instrument 86 is a spectrometer. Spectrometer 86 may be a commercially available device or alternatively a customized device that uses optical sensor 87. In some embodiments the visual input or lens of spectrometer 86 is wrapped around the glass tube or window of collector 76. As noted above, some non-optical sensors, such as conductivity sensors or specific density sensors may be used instead of or in addition to using one or more optical sensors.

A spectrometer may be used as optical measuring instrument 86 because it is an instrument that measures light intensity as a function of the wavelength of light, and is sensitive enough to detect small changes in intensity of narrow bands of frequencies. Colored molecules of substances 30 in liquid droplets 65 alter the light spectrum emanating from collector 76, and the spectrometer is, for example, set to respond to tightly windowed color bands in, for example, the 350-1100 nm range. In some embodiments spectrometer 86 has a spectral resolution of 0.07 nm and detection time of 10-100 ms. Optionally, the spectrometer uses a linear or 2D array of detectors, in which each detector location corresponds to wavelength and may be selected for attention to different reagents, uses, substances and/or calibration states.

Optionally spectrometer 86 includes color detection software to receive and analyze the readings of optical sensor 87. The color detection software is optionally configured to interpret the readings of sensor 87 to enhance the likelihood of making a correct determination of the presence of substances 30, and to minimize the likelihood of false positives. Empirical tests set the limits of the relative strengths of each wavelength needed for the receipt of a real reading. The rate of color change and the relative strengths are optionally taken into account in the software's algorithm for diagnosing false readings.

In an exemplary embodiment of the invention, the following methodology is used for hue determination. Given a color cube where the axes are red (1,0,0), green (0,1,0) and blue (0,0,1), a saturation factor angle alpha is the angle between a vector connecting the origin and a color point and the an achromatic line (0,0,0) to (1,1,1). C is a point on the achromatic line and A is the point in space of the color point.

For hue and saturation measures, the following formula may be used:

Coordinates $R_A=r$, $G_A=g$, $B_A=b$; then $[OA]=\sqrt{(r^2+g^2+b^2)}$

Coordinates $R_C=G_C=B_C=c$; then $[OC]\sqrt{3}*c$.

$[AC]=\sqrt{(r-c)^2+(g-c)^2+(b-c)^2}$;

$[OA]^2 = [OC]^2 + [AC]^2$; $[OA]^2 = r^2 + g^2 + b^2$;

$[OC]^2 = 3c^2$; then $c = \frac{r+g+b}{3}$.

$[AC]=\sqrt{(r^2+g^2+b^2-3c^2)}$, and if $L=r^2+g^2+b^2$, $a=[AC]=\sqrt{(L-3c^2)}$.

Also, $a = \sqrt{\frac{2}{3}} * \sqrt{(L - rg - rb - gb)}$.

Now, $\sin\alpha = \frac{[AC]}{[OA]} = \frac{a}{\sqrt{L}} = \sqrt{\left(1 - 3\frac{c^2}{L}\right)}$;

or $tg\alpha = \frac{[AC]}{[OC]} = \frac{a}{\sqrt{3}*c}$.

In coordinates of an HSV color cone, where the axis of the cone is an achromatic axis, the hue is a polar coordinate around the base and saturation is a distance from the achromatic axis (C) to the color point, D is the point also known as R, where hue angle is zero (red), also including Y, G, Cy, B, and M (each at 60 degree angle points), alpha is the angle between the cone wall and the achromatic axis, a is a vector connecting the axis and the base, at point A, and beta is the angle between AC and DC, so

[AC]=[DC]=a

Coordinates $$R_D = c + \sqrt{\frac{2}{3}}*a, \quad G_D = c - \frac{a}{\sqrt{6}}, \quad B_D = c - \frac{a}{\sqrt{6}}.$$

$$\cos\beta = \sqrt{\frac{2}{3}} * \frac{r - \frac{g+b}{2}}{a}$$

The hue may be determined as follows
calculation $$c = \frac{r+g+b}{3};$$

calculation $L=r^2+g^2+b^2$;
calculation $a=\sqrt{(L-3c^2)}$;
calculation $$\cos\beta = \sqrt{\frac{2}{3}} * \frac{r - \frac{g+b}{2}}{a}.$$

In an exemplary embodiment of the invention, cos beta is expected to remain unchanging until detection. Optionally, detection is based on a change in cos beta. Optionally or alternatively, different detection situations (e.g., detected substances) call for or different values of cos beta.

Spectrometer 86 (or a separate controller) may be configured to automatically alarm if a signal intensity larger than a predetermined threshold is measured within a pre-determined wavelength window, or optionally it can send a signal to controller 88 or user interface 38.

Optical sensing mechanism 82 optionally also includes an "umbrella" at the bottom of cyclone 50 to modulate pumps 60. In this way, the rate at which collector 76 fills with droplets 65 can be adjusted (e.g., manually or automatically) to ensure that there is a fixed, predetermined and/or minimal volume of liquid in collector 76 at the time of measurement by spectrometer 86.

Figure 9:
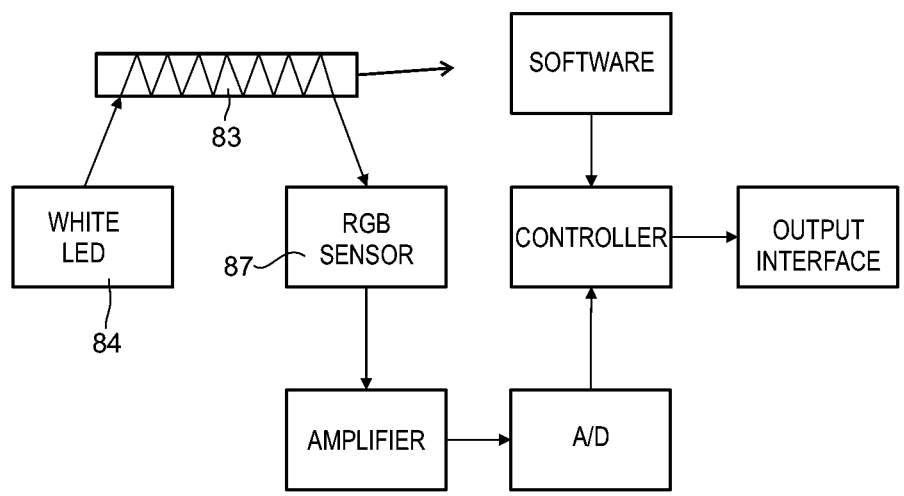
FIG. 9 is a block diagram illustrating operation of a reaction sensing mechanism of the substance detector of FIG. 1, in accordance with an embodiment of the invention.

FIG. 9 is a block diagram illustrating operation of optical sensing mechanism 82, in accordance with an exemplary embodiment of the invention. A white light from an LED in light source 84 is projected at the fixed volume of liquid in collector 76 at a specific angle. The light passes through the solution and is received in a rectangular window, where it passes through optical fiber 83 to optical sensor 87. Optionally, the light travels in a zigzag path along the collector (e.g., using total internal reflections or regular reflections) or other suitable channel, so that the actual path traveled by the light is made longer and any difference in spectral absorption is amplified. In an exemplary embodiment of the invention, the signal from the sensor is amplified, converted to a digital signal and processed by a controller, using software, to generate an indication on an output interface. Other processing methods, such as hardware only and/or analog only, maybe used.

It should be noted that in some embodiments of the invention, the detection is on static collected fluid. In other embodiments, the detection is continuous as the fluid leaves the cyclone. Optionally, the detection is started once sufficient fluid is collected and continued until the fluid is exhausted or below a threshold.

In some embodiments, the probability of detection of substance detector 20 is 0.9, and the false alarm rate is less than 0.05.

Reaction sensing mechanism 82 of substance detector 20 may employ any suitable detection system and method, and is accordingly not restricted to optical or color change. Some examples of alternative chemical reaction and detection methods are gas chromatograph/surface ionization, gas chromatography/mass spectrometry, gas chromatograph/ion mobility spectrometry, field ion spectrometry, photoacoustic spectroscopy, and gas-phase, infrared spectroscopy detection methods. In embodiments that use detection methods based on a different principle than optical or color change, other types of measuring instrument 86 and sensor 87 may be used as appropriate, and light source 84 might not be needed.

4. Sensitivity and Performance (i) Speed of Detection

In some embodiments of the invention, substance detector 20 detects the presence of substances 30 in an air sample in a time of 4 to 12 seconds.

Example

In an application of an embodiment of the invention, standard explosive materials in a concentration of $10^{-9}$ g explosive/ml of aerosol were spread in a closed room having 30 cubic meters of air space. Substance detector 20 was activated in order to detect the presence of the explosives. After 8 seconds the device detected the presence of the explosives, as a color reaction appeared in the liquid sample and an alert siren was turned on.

(ii) Sensitivity of Detection

Substance detector 20, in some embodiments, is capable of relatively high sensitivity in its ability to detect tiny or minute quantities of explosive or other materials. The sensitivity is optionally a result of sensitive chemical reactions with the reagents, use of optional sensor 87, and the relatively high concentration of substances 30 in collected droplets 65 in collector 76. In some embodiments the concentration of substances 30 is on the order of one million times higher than the concentration in air.

In some embodiments of the invention, substance detector 20 can detect the presence of an explosive compound or substance 30 present in a concentration of 0.5 to 1.0 ng/ml (nanogram per milliliter).

Example

A laboratory analysis was performed to determine the sensitivity of the optical detection method used by optical reaction mechanism 82 in an embodiment of the invention. In the analysis, different concentrations of NO compound were measured at a fixed wavelength, two measurements for each concentration, at 1, 2, 4, 8, 16, and 32 ng/ml. The results showed that even at the lowest concentrations of 1 and 2 ng/ml, a signal was obtained that was distinguishable above background noise, for a light path of 1 cm in a spectrometer. As concentration increased, absorption increased linearly. A detector that can positively detect an absorption difference of 0.001 will allow achieving the limit for NO compound detection (1 ng/ml). In an exemplary embodiment of the invention, the light path (along which spectral differentiative absorption takes place) is longer than 1 cm, for example, being 3 cm, 5 cm, 10 cm, 20 cm or more or intermediate values. A detection limit of, for example, 0.05-0.1 ng/ml is thereby expected, if, for example, 10 ml of fluid is used.

(iii) Probability of Detection

As noted above, in some embodiments of the invention, the probability of detection is 0.9 and the false alarm rate is less than 0.1.

In some embodiments of the invention, certain optional modifications or enhancements may be implemented to assist in raising the probability of detection. These include any one or combination of the following: 1) the use of high performance spectrometers 86 which can detect less than 0.07 nm change in the transmission or absorption of the liquid to the incident wavelengths, 2) the use of (decreased) concentrated sample volumes in collector 76 (e.g., more concentration, less volume), 3) effective means to minimize the evaporation rate of the fluids by either lowering the operating temperature or recondensing the vapors, and/or 4) using reagents that are sensitive to the presence of small amounts of explosives by the use of, for example cascade dual reactions and/or novel colorimetric techniques.

False alarms, or the false identification by substance detector 20 of the presence of substances 30 when they are actually not present, will occur in some instances. One reason is that molecules, particles, and/or vapors that are not a threat will be absorbed into aerosol droplets 65. Some of these substances may react with some of the reagents, which would result in a color change and false positives. Another reason is that background molecules in the liquid droplets 65 may produce a broad light spectrum that overlaps across the windows of interest. Alternatively, the background molecules might produce a large response in a neighboring area of the spectrum whose tail might overlap into the window of interest.

In some embodiments of the invention, certain optional modifications or enhancements may be implemented to assist in lowering the false alarm rate. These include any one or combination of the following: 1) tuning the assay wavelength to occur at a narrow range, i.e. discarding any color change outside the window wavelength that can be caused by other materials, 2) performing multiple data scanning and integration for increased reliability, and 3) use of dual or triple redundant multicolor assays. Optionally, such changes are provided by changing settings, changing software and/or changing the detector.

Example

In a series of experiments, RDX and TNT in concentrations of 1000, 100, 50 and 10 ppm and various volumes were injected into a detector system as described herein. No false detections were created. Some experimental results were corrupted by an interaction between the solvent used (CAN—atcetonitril) and the composition of the cyclone itself. In an exemplary embodiment of the invention, the plastics used in the cyclone will be non-reactive with the reagents selected. In some cases more than one cyclone will be provided so different reagents will be used with different cyclones. Optionally, for example as described below, a replacement module comprises a cyclone and reagents suited therefore.

Of 28 injections of 0.1 ml of TNT at 100 ppm, only 3 were not detected; giving a detection probability of 90% for a 10 microgram sample. Of 28 injections of 0.1 ml of RDX at 100 ppm, only 2 were not detected; giving a detection probability of 93% for a 10 microgram sample. TNT at 10 ppm and 50 ppm was not detected. RDX at 10 ppm was detected in all four tries thereof at 0.3 ml, but not at 0.2 ml, giving a good detection of 3 micrograms. 5 micrograms RDX were detected with a probability of 75-80% (from 20 injections of 0.1 ml of 50 ppm or 0.05 ml of 100 ppm, with 15 positive, and 5 negative including 2 malfunctions). Reaction times were 5-10seconds.

5. Exemplary Setup and Daily Operation (i) Installation

Substance detector 20, in some embodiments, may be positioned at an inspection site so that air inlet 34 is within range of designated area 28. The size of this range is related to the strength of airstream 44, which in turn is directly related to the strength of the vacuum created by air compressor 46.

For example, in the exemplary security embodiment of FIG. 1, using an air compressor of 50-70 W strength, substance detector 20 can be positioned so that air inlet 34 is within about 0.1-2 meters of designated area 28 and is expected to produce adequate results.

(ii) Calibration

Calibration of optical reaction mechanism 82 may be carried out as follows. Upon first operation of substance detector 20, the system is loaded with the reagents to be used. The system is then run in a clean environment, without exposure to any of the suspicious materials that are to be detected. The strength of the readings measured by spectrometer 86 in each of the three color bands is measured and taken as a calibration or reference point.

Subsequently, upon commencement of active operation of substance detector 20 and the examination of suspicious materials, the measuring instrument software performs a comparison between the readings received and the reference point in the three color fields, and signals when the color of the solution turns from transparent to colored (particularly various shades of red).

(iii) Modes of Operation

Substance detector 20, in some embodiments of the invention, operates in an automatic mode that enables a continuous stream of objects or people to be scanned without operator intervention, until a substance of interest is detected.

(iv) Exemplary Daily Set-Up

The consumables used by substance detector 20, in some embodiments, are the colorimetric reagents and solvent or water used for fluid spray 65. Also, where swab or wipe samples are taken, disposable sample traps may be used.

Prior to operation of substance detector 20, the operator will check the water or solvent levels in receptacle 54, the reagent levels in each of the receptacles 58, and re-fill them as appropriate. In cases where solid reagent 80 is used, the operator will also periodically check the condition of the material for wear and replace it when necessary. In some embodiments of the invention, in which substance detector 20 operates seven days a week for sixteen hours a day, for example, solid reagent 80 in the form of a zinc rod measuring several cm in length is selected so it will require replacement after approximately 15 days to 1 month of use.

(v) Exemplary User and Operator Experience

Substance detector 20, in some embodiments, allows for relatively easy operation by the operator. As noted, for maintenance the operator only needs to regularly check and refill consumables such as water, solvent, and reagents. In some embodiments of the invention this activity by the operator will take place once a day, usually at the commencement of the day's activity. In some embodiments operator checking and refill may occur more or less frequently, depending on the extent of use at the particular location.

In cases where objects rather than people are being scanned, such as for example luggage, a live operator does not need to be in attendance. The system can call the operator if a suspicious article of luggage is identified.

In cases where people are being scanned and it is desired to take swab samples, an operator may be needed to attend to take the samples and feed them to the device. In cases where swab samples are not taken, an operator may optionally not attend, but it still may be advisable to ensure that persons do not evade detection by trying to sneak past designated area 28. Alternatively, instead of an operator it may be possible in some situations to keep a police officer or other security person at the site. A security person would be advisable to have at close proximity in any event, to apprehend or investigate a person who sets off the alarm. In this way costs of operation could be minimized without loss of security.

From the perspective of a person being scanned, such as a person hurrying through an airport, substance detector 20 can have the benefit of being relatively fast and virtually non-invasive. In many cases the person only needs to get in line, step forward for a few seconds, and then move on. If swab samples are being taken then the person will experience a minimal degree of physical contact with the operator. Substance detector 20 will produce some noise, primarily from air compressor 46, at a level approximately that of a vacuum cleaner. In some embodiments airstream 44 will be felt as a gentle breeze and will not be disturbing.

In an exemplary embodiment of the invention, substance detector 20 is safe to operators, people being scanned, and/or the environment. While solvent may be used in some embodiments for fluid spray 64, it is collected inside the machine or safely conducted away from the screening area.

Figure 10:
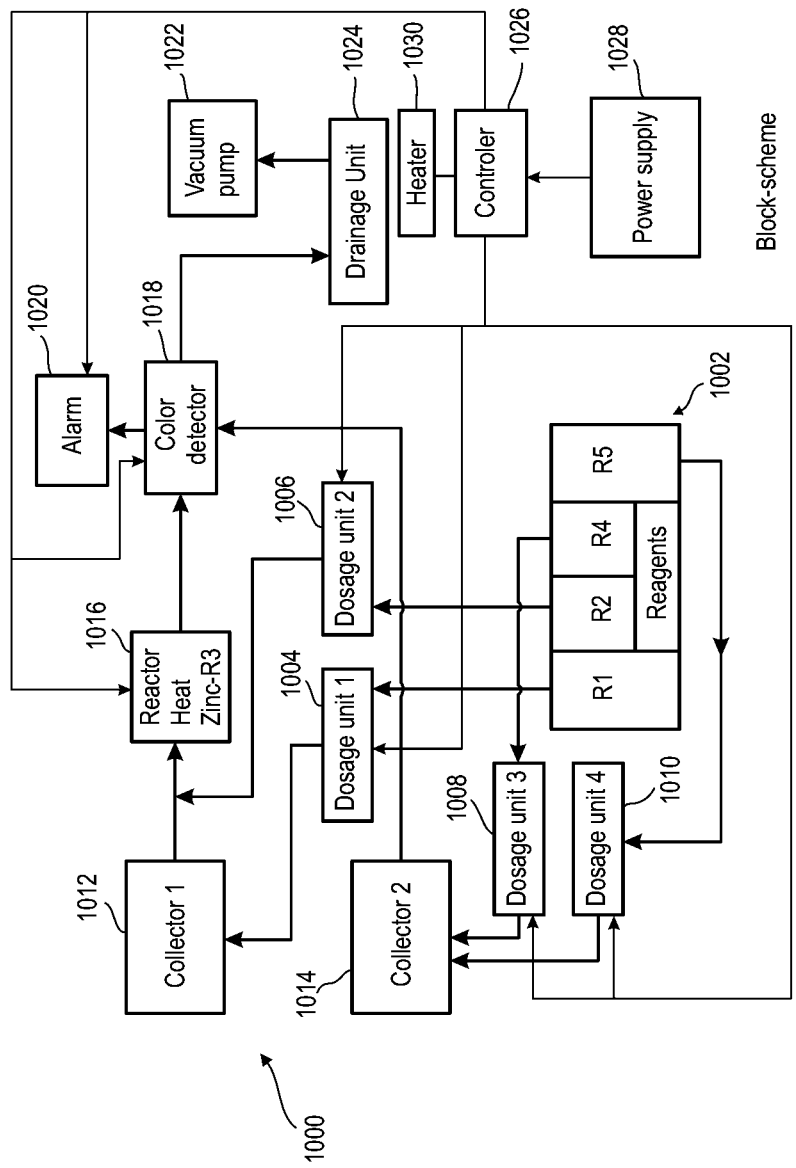
FIG. 10 is a block diagram of an exemplary detecting system, in accordance with an exemplary embodiment of the invention.

FIG. 10 is a block diagram of an exemplary cyclone based substance detector 1000, in accordance with an exemplary embodiment of the invention. Thick lines show fluid flow and thin lines show control/data/power flow.

A reagents unit 1002 can include a plurality of reagent containers. One or more metered pumps 1004, 1006, 1008 and 1010 may be used to provide the reagents to cyclones (not shown, but two optionally provided), for collection after mixture with air samples in a first collector 1012 and a second collector 1014. It is noted that a greater or smaller number of cyclones may be provided.

The first collector 1012 may convey collected liquid to a solid reagent (zinc) 1016. Liquid from both collectors may be detected by a single color detector 1018 (e.g., an RGB detector), which can trigger an alarm 1020. Fluid is then optionally drained via a drainage unit 1024, optionally powered by a vacuum pump 1022.

In an exemplary embodiment of the invention, device 1000 is controlled using a controller 1026.

A power supply 1028, for example, a rechargeable battery, may be shared among multiple device components.

Optionally, the cyclone, reagents, collectors and/or other parts of device 1000 are heated, for example, using one or more heaters 1030, for example, to 50, 70, or 90 degrees Celsius or intermediate, smaller or higher temperatures.

In an exemplary embodiment of the invention, detector 1000 is self cleaning (e.g., by the continuous flow of reagents and air therethrough. Optionally, detector 1000 includes an optional cleaning cycle in which a cleaning fluid or additional reagents flow, without sampling, or in which a filter is placed over an air intake and/or air intake is linked to air exhaust, so that no contaminated air can enter.

In an exemplary embodiment of the invention, detector 1000 is configured for modular field replacement of parts, for example, when components get used up or contaminated. In one example, the reagents and/or misting fluid are provided in a cartridge which can be replaced as a whole. Optionally or alternatively, the cyclone body or a lining thereof is provided as a cartridge. Optionally or alternatively, the reagents, misting fluid and/or the cyclone are provided as a cartridge. Optionally or alternatively, the detector and/or solid reagent are provided as a replacement cartridge, optionally as part of a different cartridge. Optionally, pumps, valves, electronics and/or software are permanent. Alternatively, at least one of such items is part of a cartridge. For example, all tubing may be part of such a cartridge. Optionally, any pumping and valving are, for example, using a peristaltic pump, which does not contact the flowing fluids. Optionally or alternatively, instructions identifying the reagent constants and/or detector calibration and/or cyclone parameters are digitally or electronically readable off a replacement cartridge. Optionally or alternatively, a power source, such as a battery, is replaceable and/or part of a cartridge. Optionally, a cartridge is designed to provide a certain number of tests. Such design may affect, for example, reagent volume and/or power source capacity.

In an exemplary embodiment of the invention, for such cartridge replacement, fast connectors are used. For example, if reagents are part of a cartridge, tubing form the reagent compartments can all be pointed in a same direction and, for example, snap-fit, friction-fit or otherwise interlock when inserted. Optionally, a user tightening step is performed, for example, using a screwdriver or using a knob which locks or unlocks fluid, gas and/or electrical connectors. Optionally, connectors are via an auxiliary board or directly to a main system board, depending on the assembly in the device.

Optionally, detector 1000 includes multiple cyclones, for example, for detecting using incompatible reagents and/or device parameters. In an exemplary embodiment of the invention, detector 1000 is portable, optionally weighting less than 20 Kg, less than 10 Kg, less than 5 Kg or intermediate weights. Optionally or alternatively, the volume of detector 1000 is less than 100 liter, less than 50 liter, less than 20 liter or intermediate volumes. Optionally, a maximum dimension of detector 1000 is 50, 40 or 30 cm or less.

Figure 11A:
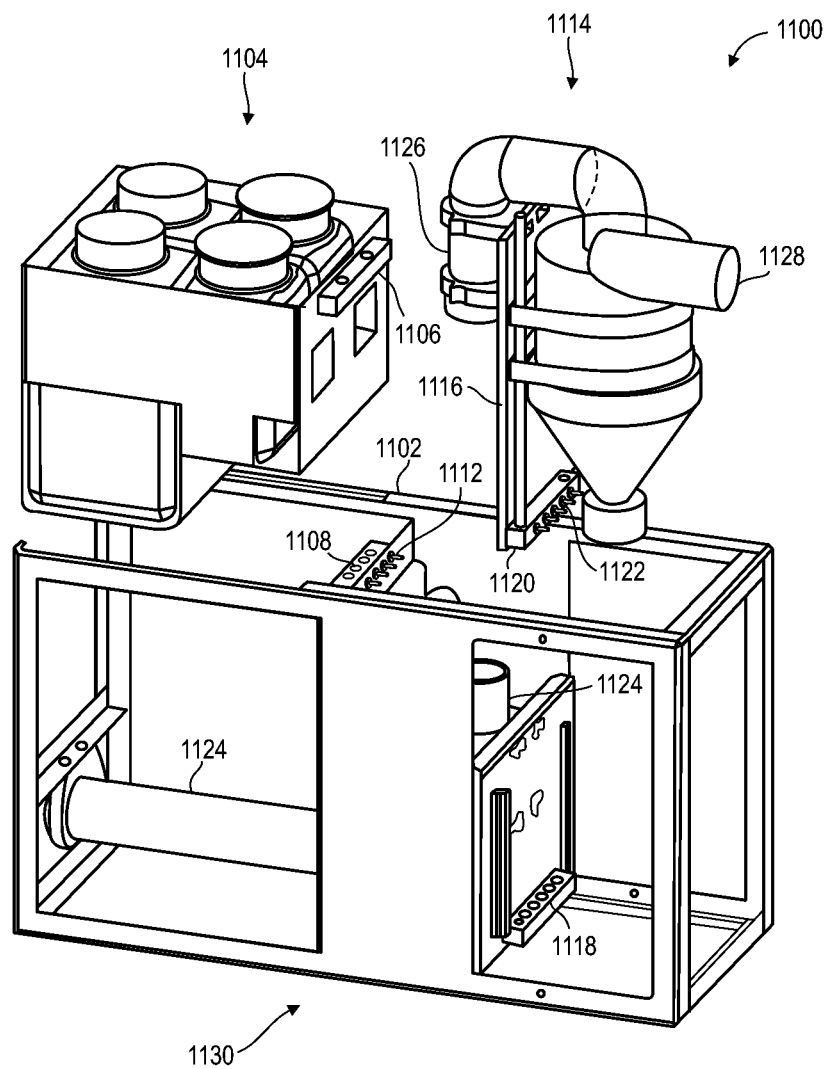
FIG. 11A is a side perspective exploded view and FIG. 11B is a side perspective assembled view of a detector system in accordance with an exemplary embodiment of the invention.
Figure 11B:
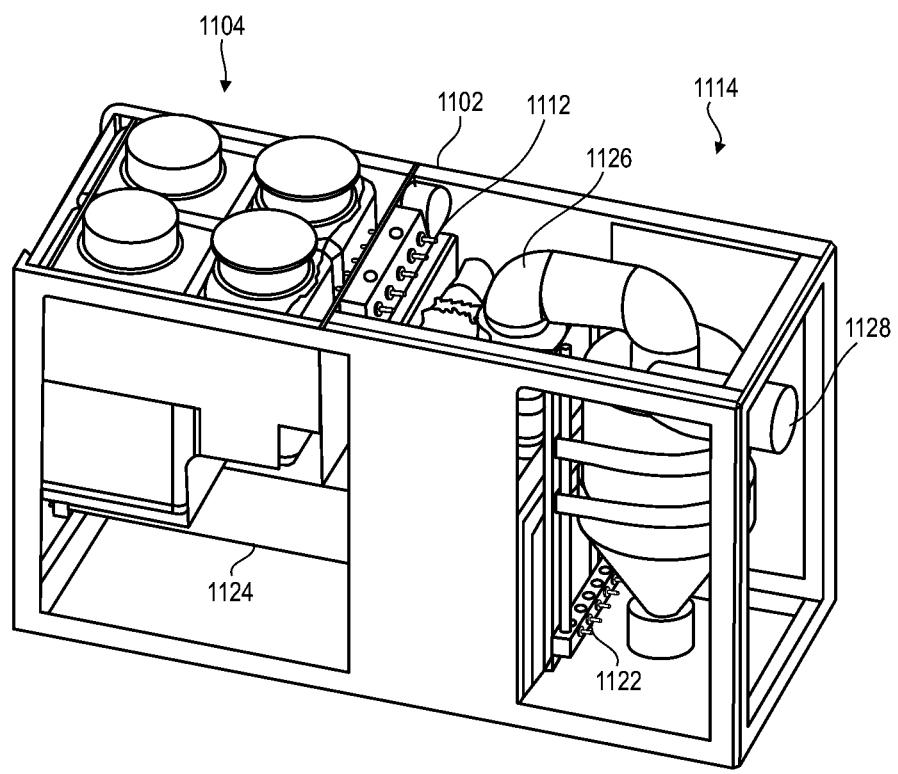

FIG. 11A is a side perspective exploded view and FIG. 11B is a side perspective assembled view of a detector system 1100 in accordance with an exemplary embodiment of the invention.

As shown, a reagent module 1104 and a cyclone module 1114 can be quickly attached to and/or removed from a frame 1102.

In an exemplary embodiment of the invention, the connection utilizes fast connectors, for example, snap connectors and/or friction connectors. In the example shown, for reagents unit 1104, an array of fluid connectors 1106 mates with an array of fluid connectors 1108. A plurality of nipples 1112 serves to connect to tubing (not shown, for clarity).

Similarly, for cyclone 1114, an array of fluid connectors 1118 may connect to an array of connectors 1120. In an exemplary embodiment of the invention, a board 1116 includes electronics. Optionally or alternatively, board 1116 includes fluid pathways to the various reagent ports. Alternatively, an array of nozzles 1122 connects to tubes (not shown) for fluid flow within the cyclone unit. In an exemplary embodiment of the invention, an exhaust pipe 1126 of the cyclone snap fits an exhaust pipe 1124 of frame 1102. A reference 1130 generally indicates a location of non-replaceable components, such as a battery, circuitry and/or an air pump. An inlet 1128 may snap connect to a faceplate input.

Optionally or alternatively to using fast connectors, one or more connectors May require tightening, for example, using a suitable tool. Optionally, cyclone unit 1114 and/or reagent unit 1104 can be locked or unlocked into frame 1102. Optionally, such locking/unlocking is a fast locking/unlocking. Alternatively, one or more screws are used for such tightening.

(vi) Alternative Cyclone Designs

As can be appreciated, various device components can be designed differently from what is shown herein. For example, the cyclone design may be changed, for example, to reduce escape of water droplets.

Figure 12:
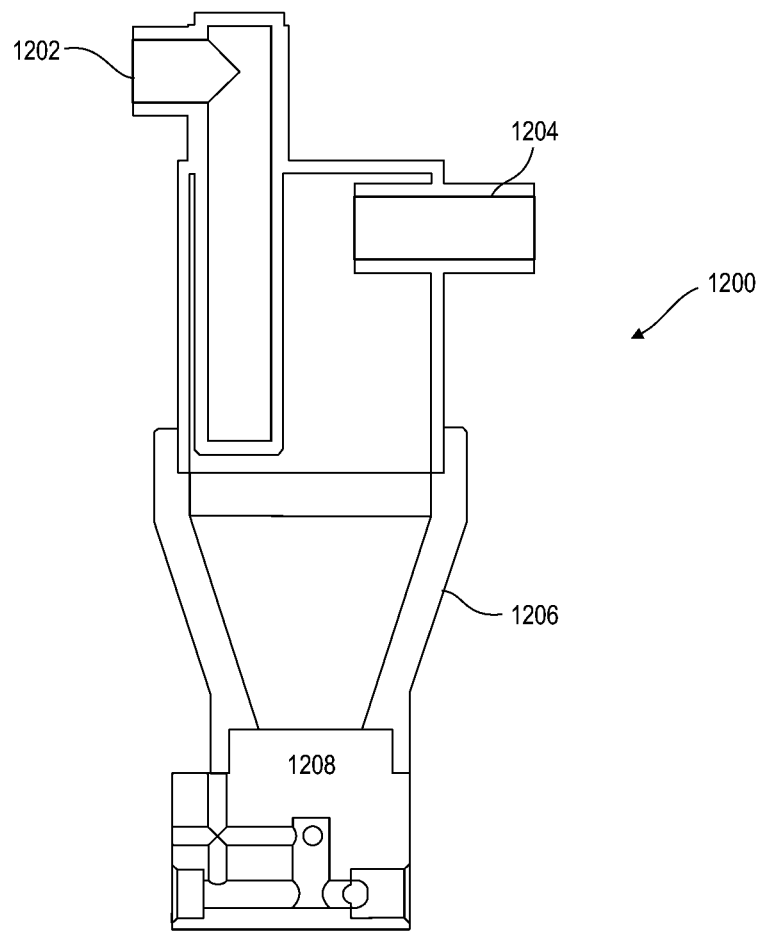
FIG. 12 is a side cross-sectional view of a cyclone design, in accordance with an exemplary embodiment of the invention.

FIG. 12 is a side cross-sectional view of a cyclone design 1200, in accordance with an exemplary embodiment of the invention. In this design, an inlet 1204 injects samples into a cyclone body and the cyclone is exhausted using an exhaust 1202. Optionally, exhaust 1202 is positioned, for example, near a conical section 1206 of cyclone 1200 and/or to a side thereof, so that droplet exit is reduced. A collector 1208 collects droplets as described above.

FIGS. 13A-13E are engineering drawings of a cyclone design, in accordance with an alternative exemplary embodiment of the invention. FIG. 13A is a front view; FIG. 13B is a side view; FIG. 13C is a front cross-sectional view; FIG. 13D is a perspective view and FIG. 13E is a top view.

6. Chemistry of Exemplary Applications (i) Explosives

The detection of explosives can be technically difficult. As noted, some explosives such as plastic explosives have extremely low vapor pressures, particularly when sealed inside luggage. The vapor pressure may be as low as parts per billion or trillion. Explosives also come in different types, each of which in most cases has to be detected by the system to be effective.

Explosives are generally classified as belonging to one of the following four groups:

1) Nitroaromatics (also known as "Group A" explosives), include TNT, Tetryl, TNB, DNT, picric acid and its salts;

2) Nitrate esters and nitramines (also known as "Group B" explosives), include most plastic types of explosives such as C4 and Semtex H, and also include Nitroglycerine, RDX, PETN, Nitrocellulose,and smokeless powder;

3) Nitrate-based or Inorganic Nitrates includes ANFO (ammonium nitrate-fuel oil), commercial and improvised explosives based on inorganic nitrates (e.g ANFO), black powder, flash powder, gun powder, potassium chlorate and nitrate, sulfur (powder), ammonium nitrate (both fertilizer and aluminum); and 4) Peroxide-based explosives(or "peroxides") include TATP (Tri Acetone Tri Peroxide), and HMTD. These are powerful explosive substances that can be prepared from over the counter ingredients.

The inventors have selected reagents R1 and R2 that are suited for the detection of explosives from groups 1 and 2. Other reagents may be selected, for example, as manufactured by the Mistral corporation and/or optionally optimized for the detection times and color sensitivity of the detector.

Reagent 1 (R1)

The ingredients of R1 and their relative amounts are as follows:

| Name | Formula | g | ml | CAS No. |
|---|---|---|---|---|
| Potassium hydroxide | KOH | 2 | — | 1310-58-3 |
| Methyl alcohol | $CH_3OH$ | — | 5 | 67-56-1 |
| Iso-propyl alcohol (2-propanol) | $(CH_3)_2CHOH$ | — | 15 | 67-63-0 |
| Dimethylsulphoxide | $(CH_3)_2SO$ | — | 80 | 67-68-5 |

To prepare R1, place the KOH in a vessel, add methanol and stir with a magnetic mixer. Dissolve, preferably chilled, with the vessel closed such as by cork. Add the isopropyl and DMSO.

Reagent 2 (R2)

The ingredients of R2 and their relative amounts are as follows:

| Name | Formula | g | ml | CAS No. |
|---|---|---|---|---|
| Sulfanilamide | $NH_2C_6H_4SO_2NH_2$ | 2.0 | — | 63-74-1 |
| Ammonium Sulfamate | $NH_4OSO_2NH_2$ | 0.5 | — | 7773-06-0 |
| N-(1-Naphthyl) ethylenediamine dihydrochloride | $C_{10}H_7NHC_2H_4NH_2 \cdot 2HCl$ | 0.3 | — | 1465-25-4 |
| Phosphoric Acid | $H_3PO_4$ | — | 20 | 7664-38-2 |
| Water | $H_2O$ | — | 80 | 7732-18-5 |

To prepare R2, add the first three ingredients above in a vessel and then add the phosphoric acid and water and dissolve while stirring magnetically and heating slightly (40° C.).

Reagents 1 and 2 can be used to detect most explosive groups. For example, most explosives contain aromatic compounds with RAr—NO2, NO2-, and NO3-groups. These compounds are typical in standard explosives, as well as improvised explosives such as chlorates and bromates (black powder and fertilized components used for explosive fabrication). Reagent 1 determines all R—NO2 groups, and reagent 2 determines NO2-, NO3-ions (all NO3-groups are converted into NO2-groups).

As noted, group 3 explosives may be detected by exposing the liquid containing explosive particles to a zinc surface from solid reagent 80. The surface may be heated to improve the efficiency of the chemical reaction. Optionally, a heater is provided, for example, a hot air source aimed at the collector, or a heater which heats the rod. Optionally or alternatively, the air and/or reagents and/or fluids and/or cyclone body are heated, for example, using a resistance heater, or using contact with a hot fluid, such as hot water or oil and/or solid heatsink which is otherwise heated and/or optionally maintained at a desired temperature using a thermostat.

In some embodiments of the invention, commercially available reagents can be used for the detection of group 3 explosives such as chlorates and perchlorates, and group 4 explosives such as improvised explosives based on TATP and HMTD.

In some embodiments of substance detector 20, the reagents are used with a different concentration and temperature than standard atmospheric pressure and room temperature.

(ii) Narcotics/Drugs

Well known reagents may be used for narcotics detection. For example The identification of Cocaine (by spot-test) can be carried out using the above cyclone apparatus by using Cobalt Thiocyanate (Cobalt chloride+ammonium thiocyanate in water) to develop a blue color (blue precipitate).

Barbiturates may be identified using a Dillie-Kopanyi reagent (Cobalt acetate in methanol with glacial HOAc. and isopropylamine in methanol) to develop a red violet color.

Morphine may be identified by using Ferric chloride (in water) to develop a blue-green color. ["Forensic Science Handbook", Vol. II (pg. 122) by Richard Saferstein, 1998]. Sets of reagents are sold, for example, by ODV, Inc. and by NIK Inc.

Following is a list of reagents and drugs they test for from ODV, Inc., 13386 International Parkway, Jacksonville, Fla. 32218. These are generally provided in 0.5 ml ampoules ("NARCOTEST®" and "NarcoPouch®") but may be packaged differently for some embodiments of the invention:

The numbers are part number and pouch number, if applicable.

7601 901 Mayer's for General Narcotic Compounds, contains potassium tri-iodo mercurate 1% in water 0.5 ml

7602 902 Marquis for Heroin/Amphetamines, contains 37% formaldehyde solution 2% In concentrated sulfuric acid 0.5 ml

7603 903 Nitric Acid to Differentiate Heroin from Morphine, contains concentrated nitric acid 0.5 ml

7604 Cobalt Thiocyanate for Cocaine, contains (bottom ampoule) cobalt thiocyanate 5% in water 0.5 ml; (top ampoule) Stannous chloride dihydrate 4% and hydrochloric acid 8% in water 0.5 ml 904B for Cocaine Salts & Base Reagent, contains (left ampoule 0.6 ml) cobalt thiocyanate 1% and 1% boric and tartaric acids and glycerine 50%; (middle ampoule. 02 ml) concentrated hydrochloric acid; (right ampoule 0.5 ml) chloroform

7605 905 Dille-Koppanyi for Barbiturates, contains (bottom ampoule) cobaltous acetate 0.1% and glacial acetic acid 0.2% in isopropanol and water 0.5 ml; (top ampoule) Isopropylamine 5% and isopropanol 0.5 ml

7606 906 Mandelin for Methadone/Amphetamines, contains ammonium vanadate 0.009% in concentrated sulfuric acid 0.5 ml

7607 907 Ehrlich's (modified) for LSD, contains (bottom/left ampoule) paradimethylaminobenzaldehyde 5% in isopropanol 0.5 ml; (top/middle ampoule) Concentrated hydrochloric acid 0.5 ml; (right ampoule of 907) concentrated phosphoric acid

7608 Duquenois for Marijuana, contains (bottom ampoule) vanillin 2% and acetaldehyde 0.5% in ethanol 0.5 ml; (top ampoule) concentrated hydrochloric acid 0.5 ml 908 Duquenois-Levine for Marijuana, contains (left ampoule) vanillin 2% and acetaldehyde 0.5% in ethanol 0.5 ml; (middle ampoule) concentrated hydrochloric acid 0.5 ml; (right ampoule) chloroform 0.7 ml

7609 909 KN Reagent for Marijuana, contains (bottom ampoule) Fast Blue B salt 0.31% in trichloroethylene 0.5 ml; (top ampoule) sodium hydroxide 10% in water 0.5 ml

7613 for Cocaine Free-Base, contains (bottom ampoule) cobalt thiocyanate 3% in glacial acetic acid 10% and water 0.5 ml; (top ampoule) stannous chloride dihydrate 4% and hydrochloric acid 8% in water 0.5 ml

7614 914 Methaqualone for PCP, contains (bottom ampoule) cobalt thiocyanate 2.5% and water 0.2 ml; (top ampoule) phosphoric acid 0.2 ml (Note: 914 is 0.3 ml both ampoules)

922 for Opiates, contains (left ampoule) concentrated sulfuric acid 0.4 ml; (right ampoule) 0.5% ammonium molybdate in sulfuric acid 0.5 ml

7623 923 for Sodium Nitroprusside, contains aqueous solution of 2% sodium carbonate and sodium nitroprusside

7624 924 Mecke's (Modified), for Heroin, contains (left ampoule) concentrated sulfuric acid 0.5 ml; (right ampoule) 0.6% selenious acid in concentrated sulfuric acid 0.5 ml

7625 925 for Valium, contains (bottom ampoule) 3% potassium hydroxide in methanol 0.2 ml; (top ampoule) 0.05% m dinitrobenzene in isopropanol 0.5 ml

7626 926 for Talwin, contains 0.5% ammonium molybdate in sulfuric acid 0.5 ml

7627 927 for Ephedrine, contains (bottom ampoule) 1% copper sulfate+1% glacial acetic acid in water 0.5 ml; (top ampoule) 8% NaOH in water 0.2 ml

7628 928 for GHB, contains 48% ethanol in water plus <1% organic dyes bromocresol green, methyl orange, and aniline HCl (iii) Poisons Reagents for detecting poisons are well known and may be used in the above cyclone. For example, free cyanide can be detected using p-nitrobenzaldehide and o-dinitrobenzene to give purple color ["Semi Quantitative Spot Test of Cyanide", by J. A. D Favero, *Analytical Sciences*, Vol. 19, #8, (pg. 1139), 2003].

(iv) Pesticide Residues

Reagents for detecting pesticides are well known and may be used in the above cyclone. It is noted that also multi-step reagents systems can be used, by controlling droplet travel time in the cyclone so that a desired delay between steps is achieved.

As used herein the term "about" refers to ±10%.

The terms "comprises," "comprising," "includes," "including," "having" and their conjugates mean "including but not limited to."

As used herein, the singular forms "a," "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicated number and a second indicated number and "ranging/ranges from" a first indicated number "to" a second indicated number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. An apparatus for detecting substances in an air sample, the apparatus comprising:
    a source of air pressure differential;
    a cyclone connected to the source of air pressure differential;
    an air input port connected to the cyclone, to receive the air sample;
    a substance output port connected to a bottom of the cyclone, to receive the substances;
    at least one reagent input port configured to inject at least one reagent into the cyclone;
    a discharge port configured to remove the substances from said apparatus, said substance output port disposed between said cyclone and said discharge port;
    a detector located at the substance output port, to detect a chemical change in at least one of the substances and the at least one reagent;
    a first exhaust channel configured to direct air towards a first air outlet port at an upper section of said cyclone; and
    a second exhaust channel extending towards the bottom of said cyclone and positioned to remove air from the bottom of said cyclone and to direct the air toward a second air outlet port at the upper section of said cyclone.

2. An apparatus according to claim 1, wherein the at least one reagent input port comprises a first reagent input port connected to one part of the cyclone and a second reagent input port connected to a second part of the cyclone.

3. Apparatus according to claim 1, further comprising a damper configured to redirect droplets from said second exhaust channel toward said substance output port.

4. Apparatus for detecting at least one substance in an air sample, the apparatus comprising:
    a source of air pressure differential;
    a cyclone connected to the source of air pressure differential;
    an air input port connected to the cyclone, to receive the air sample;
    a substance output port connected to a bottom of the cyclone, to receive the at least one substance;
    a material input port configured to disperse into air within the cyclone a first finely separated material so that the first finely separated material mixes with said sample in the air within the cyclone to form droplets;
    a detector located at the substance output port, to detect a chemical change in at least one of the at least one substance and the first finely separated material;

a first exhaust channel configured to remove air from an upper section of said cyclone; and a second exhaust channel extending towards the bottom of said cyclone and positioned to remove air from the bottom of said cyclone;

wherein said apparatus is configured to create an airflow path within said cyclone, said airflow path including first and second portions, said cyclone configured to direct air within said first portion of said airflow path toward said substance output port, said first airflow portion including a rapid airflow in an upper section of said cyclone wherein the droplets are swung outward toward an inner wall of the cyclone and fall towards said substance output port and a slow airflow wherein the droplets are directed toward said substance output port, wherein air in said first portion is removed from said cyclone by said first exhaust channel and is directed toward a first air outlet port at an upper section of said cyclone;

said cyclone further configured to direct air within said second portion of said airflow path along said second exhaust channel toward a second air outlet port at an upper section of said cyclone, said second portion of said airflow path being at least partly disposed within said second exhaust channel.

5. Apparatus according to claim 4, wherein said finely separated material is a spray of a fluid to which said at least one substance adsorbs.

6. Apparatus according to claim 5, said apparatus configured such that the fluid engages in a chemical reaction with the at least one substance while airborne.

7. Apparatus according to claim 4, wherein said material input port is into the cyclone.

8. Apparatus according to claim 4, arranged so that said finely separated material is driven to a material collector of said cyclone and from said collector said first finely separated material travels to said substance output port.

9. Apparatus according to claim 8, wherein said collector comprises a wall of said cyclone.

10. Apparatus according to claim 4, configured to drive said at least one substance to said substance output port.

11. Apparatus according to claim 4, wherein said cyclone comprises a first section with faster airflow and a second section with slower airflow.

12. Apparatus according to claim 11 comprising two air outlet ports, one for each of said first and second sections.

13. Apparatus according to claim 4, comprising at least one fluid reagent port into said cyclone.

14. Apparatus according to claim 13 wherein said fluid reagent port is a flowing port.

15. Apparatus according to claim 4, comprising a solid reagent input port.

16. Apparatus according to claim 4, comprising a controller which times dispersing by said material input port and activates detecting by said detector.

17. An apparatus according to claim 4, wherein said cyclone is configured so that a travel time of a sample from when it first interacts chemically with contents of the cyclone and when it reaches said detector is within a time range associated with a chemical interaction between the at least one substance and the first finely separated material.

18. An apparatus according to claim 4, further configured to disperse into the cyclone a second material so that the second material mixes with said sample in the air within the cyclone;

wherein said cyclone is configured so that a travel time of a sample from when the sample first interacts chemically with the first finely separated material and when it second interacts chemically with the second material in said cyclone is within a time range associated with chemical interactions between the at least one substance and at least one of the first finely separated material and the second material.

19. Apparatus according to claim 4, wherein said detector is an optical color detector which detects an interaction of light with at least one of the at least one substance.

20. Apparatus according to claim 4, said apparatus further comprising a reagent container, wherein at least one of said cyclone and said container and said detector is configured for field replacement.

21. Apparatus according to claim 4, wherein said material input port is fluidicly connected to a container of reagent.

22. Apparatus according to claim 4, wherein said substance output port is configured to control a volume of material in said substance output port.

23. An apparatus according to claim 4, said apparatus further comprising:

an air passageway, said air input port connected to said passageway, to receive the air sample, said substance output port connected to said passageway, to receive the at least one substance, a material input port configured to inject a material into said passageway to chemically interact with the at least one substance, and a station for processing the at least one substance after the at least one substance interacts with said first finely separated material, wherein said material input port and said passageway and said source of air pressure differential are configured to provide a time of travel for said sample from said material input port to said station commensurate with said first finely separated material and processing at said station.

24. Apparatus according to claim 23, wherein said time of travel is selected from the range of 200 ms to 4 seconds.

25. Apparatus according to claim 24, wherein said time of travel is determined by at least one of an angle at which the first finely separated material is dispersed into said material input port and positioning of a slot via which the at least one substance enters said cyclone.

26. Apparatus according to claim 25, wherein said angle is in the range of 1-3 degrees.

27. Apparatus according to claim 4, wherein said a material input port is configured to sequentially disperse into air within the cyclone the first finely separated material and a second material so that said first finely separated material and second material mix with said sample in the air within the cyclone at a preselected amount of time after the first finely separated material has mixed with the sample.

28. Apparatus according to claim 4, wherein said second exhaust channel includes a tubular structure configured to carry the air along the second portion of the airflow path.

29. Apparatus according to claim 4, further comprising a damper, wherein said damper collects droplets of material in said airflow path in air exhausting from said cyclone in said second exhaust channel.

30. Apparatus according to claim 4, wherein said cyclone includes an upper section configured for airflow at a first speed and a lower section configured for airflow at a second speed, wherein the first speed is greater than the second speed.

31. Apparatus according to claim 30, wherein the second speed is one of 50%, 20%, and 10% of the first speed.

32. Apparatus according to claim 4, wherein said air input port includes a structure configured to cause an airstream to rotate in a rapid spiral within said cyclone.

33. Apparatus according to claim 32, wherein said structure includes a first section configured for receiving the air sample and a second section configured for directing the air sample from said first section into said cyclone, said second section narrower than said first section.

34. Apparatus according to claim 4, wherein said apparatus is configured to gravity feed the at least one substance along said cyclone, from said air input port to said substance output port.

35. Apparatus according to claim 4, wherein said source of air pressure differential is configured to create a flow rate of air in said cyclone of 1000 liters/minute.

36. Apparatus according to claim 4, wherein the at least one substance is contained in fluid droplets, the droplets having one of diameters in a range of from 0.1 -8 microns and diameters of about 3 microns.

37. Apparatus according to claim 4 wherein, wherein the at least one substance is contained in fluid droplets, the droplets having diameters measuring either less than 0.07 microns or more than 10 microns.

38. Apparatus according to claim 4, wherein the at least one substance is contained in fluid droplets, wherein the size of the droplets is controlled by at least one of:
   an outlet diameter of an injector, said injector configured to disperse the first finely separated material into the air within said cyclone;
   air pressure and fluid volume of said injector; and
   the flows of a pressurized air input and a fluid input in an atomizer, said atomizer configured to disperse the first finely separated material into the air within said cyclone.

39. Apparatus according to claim 4, wherein said second exhaust channel is disposed along an axis of the cyclone.

40. Apparatus according to claim 4, wherein said first and second exhaust channels include inner and outer tubular portions, said inner and outer tubular portions being concentric and configured to allow air to flow inside said inner tubular portion and between said inner and outer tubular portions, and wherein said inner tubular portion is configured to remove air from the bottom of said cyclone.

41. Apparatus according to claim 4, wherein said apparatus further comprises a damper configured to redirect droplets from within said second portion of said airflow path toward said substance output port.

42. Apparatus according to claim 41, wherein said damper is configured to redirect droplets of said first finely separated material in air exhausting from said cyclone.

43. Apparatus according to claim 41, said damper further configured to allow air within said second portion of said airflow to pass through said damper toward said second air output port.

44. Apparatus according to claim 41, wherein said damper is configured for damping air flow in at least one of said first and second portions.

45. Apparatus according to claim 41, wherein said damper includes at least one of wings and a wire mesh.

46. Apparatus according to claim 4, wherein said apparatus further comprises a damper including a filter configured to collect droplets of the first finely separated material mixed with the sample from within said second portion of said airflow path.

47. Apparatus according to claim 4, wherein said second exhaust channel includes apertures configured to allow air exhausting from the bottom of said cyclone to pass therethrough.

* * * * *